US010428377B2

(12) United States Patent
Knapp et al.

(10) Patent No.: US 10,428,377 B2
(45) Date of Patent: Oct. 1, 2019

(54) METHODS OF DETECTING LOW COPY NUCLEIC ACIDS

(71) Applicant: CALIPER LIFE SCIENCES, Inc., Hopkinton, MA (US)

(72) Inventors: Michael R. Knapp, Palo Alto, CA (US); Jill M. Baker, Redwood City, CA (US); Andrea W. Chow, Los Altos, CA (US); Anne R. Kopf-Sill, Portola Valley, CA (US); Michael Spaid, Mountain View, CA (US)

(73) Assignee: CALIPER LIFE SCIENCES, INC., Hopkinton, MA (US)

( * ) Notice: Subject to any disclaimer, the term of this patent is extended or adjusted under 35 U.S.C. 154(b) by 516 days.

(21) Appl. No.: 14/252,755

(22) Filed: Apr. 14, 2014

(65) Prior Publication Data

US 2014/0227709 A1 Aug. 14, 2014

Related U.S. Application Data

(60) Division of application No. 11/873,753, filed on Oct. 17, 2007, now Pat. No. 8,697,362, which is a
(Continued)

(51) Int. Cl.
*C12Q 1/68* (2018.01)
*C12Q 1/686* (2018.01)
(Continued)

(52) U.S. Cl.
CPC ............ *C12Q 1/686* (2013.01); *B01L 3/5027* (2013.01); *C12Q 1/6837* (2013.01);
(Continued)

(58) Field of Classification Search
None
See application file for complete search history.

(56) References Cited

U.S. PATENT DOCUMENTS 5,271,724 A 12/1993 Van Lintel
5,277,556 A 1/1994 Van Lintel
(Continued)

FOREIGN PATENT DOCUMENTS

JP 2003153692 A * 5/2003
WO 94/05414 A1 3/1994
(Continued)

OTHER PUBLICATIONS

Chiou et al. (A Closed-Cycle Capillary Polymerase Chain Reaction Machine, Anal Chem., 2001, 73(9), pp. 2018-2021, Publication Date (Web): Mar. 22, 2001).*
(Continued)

*Primary Examiner* — Aaron A Priest
(74) *Attorney, Agent, or Firm* — Day Pitney LLP

(57) ABSTRACT

Methods are provided for detecting low copy nucleic acids of interest in a sample. In one method, a sample comprising a nucleic acid of interest is aliquotted into a plurality of reaction mixtures, at least two of which are single-copy reaction mixtures. The reaction mixtures are subjected to one or more amplification reactions while flowing through a channel of a microfluidic device. At least one of the reaction mixtures is formulated in an aqueous phase of an emulsion comprising aqueous droplets suspended in an immiscible liquid. The nucleic acid of interest is present as a single copy in at least one aqueous droplet of the aqueous phase prior to performing the amplification reaction(s). Amplification is performed on the reaction mixture when it is formulated in the emulsion. The nucleic acid is continuously flowed during a plurality of steps of the method.

15 Claims, 14 Drawing Sheets

Related U.S. Application Data continuation of application No. 10/741,162, filed on Dec. 19, 2003, now abandoned.

(60) Provisional application No. 60/462,384, filed on Apr. 11, 2003, provisional application No. 60/436,098, filed on Dec. 20, 2002.

(51) Int. Cl.
    *B01L 3/00*     (2006.01)
    *C12Q 1/6837*     (2018.01)
    *C12Q 1/6851*     (2018.01)
    *B01L 7/00*     (2006.01)

(52) U.S. Cl.
    CPC .............. *C12Q 1/6851* (2013.01); *B01L 7/52* (2013.01); *B01L 2200/10* (2013.01); *B01L 2200/16* (2013.01); *B01L 2300/1827* (2013.01); *B01L 2400/0406* (2013.01); *C12Q 2531/113* (2013.01)

(56) References Cited

U.S. PATENT DOCUMENTS

| | | |
|---|---|---|
| 5,302,509 A | 4/1994 | Cheeseman |
| 5,314,809 A | 5/1994 | Erlich et al. |
| 5,375,979 A | 12/1994 | Trah |
| 5,427,929 A | 6/1995 | Richards et al. |
| 5,521,065 A | 5/1996 | Whiteley et al. |
| 5,545,531 A | 8/1996 | Rava et al. |
| 5,587,128 A | 12/1996 | Wilding et al. |
| 5,601,982 A | 2/1997 | Sargent et al. |
| 5,695,940 A | 12/1997 | Drmanac et al. |
| 5,716,825 A | 2/1998 | Hancock et al. |
| 5,741,640 A | 4/1998 | Fuller |
| 5,741,678 A | 4/1998 | Ronai |
| 5,763,175 A | 6/1998 | Brenner |
| 5,779,868 A | 7/1998 | Parce et al. |
| 5,824,516 A | 10/1998 | Collu et al. |
| 5,830,663 A * | 11/1998 | Embleton et al. ........... 435/6.14 |
| 5,842,787 A | 12/1998 | Kopf-Sill et al. |
| 5,863,502 A | 1/1999 | Southgate et al. |
| 5,869,004 A | 2/1999 | Parce et al. |
| 5,908,755 A | 6/1999 | Kumar et al. |
| 5,922,604 A | 7/1999 | Stapleton |
| 5,925,517 A | 7/1999 | Yagi et al. |
| 5,939,291 A | 8/1999 | Loewy et al. |
| 5,942,443 A | 8/1999 | Parce et al. |
| 5,955,029 A | 9/1999 | Wilding et al. |
| 5,958,694 A | 9/1999 | Nikiforov |
| 5,962,228 A | 10/1999 | Brenner |
| 5,965,410 A | 10/1999 | Chow et al. |
| 5,972,619 A | 10/1999 | Drmanac et al. |
| 6,037,130 A | 3/2000 | Tyagi et al. |
| 6,042,709 A | 3/2000 | Parce et al. |
| 6,054,270 A | 4/2000 | Southern |
| 6,083,763 A | 7/2000 | Balch |
| 6,096,499 A | 8/2000 | Kozlowski et al. |
| 6,149,870 A | 11/2000 | Parce et al. |
| 6,150,516 A | 11/2000 | Brenner et al. |
| 6,171,850 B1 | 1/2001 | Nagle et al. |
| 6,174,670 B1 | 1/2001 | Wittwer et al. |
| 6,174,675 B1 | 1/2001 | Chow et al. |
| 6,235,471 B1 | 5/2001 | Knapp et al. |
| 6,268,146 B1 | 7/2001 | Shultz et al. |
| 6,287,520 B1 | 9/2001 | Parce et al. |
| 6,303,305 B1 | 10/2001 | Wittwer et al. |
| 6,303,343 B1 | 10/2001 | Kopf-Sill |
| 6,379,929 B1 | 4/2002 | Burns et al. |
| 6,391,622 B1 | 5/2002 | Knapp et al. |
| 6,403,338 B1 | 6/2002 | Knapp et al. |
| 6,406,893 B1 | 6/2002 | Knapp et al. |
| 6,440,706 B1 * | 8/2002 | Vogelstein et al. ........... 435/91.2 |
| 6,440,722 B1 | 8/2002 | Knapp et al. |
| 6,444,461 B1 | 9/2002 | Knapp et al. |
| 6,482,364 B2 | 11/2002 | Parce et al. |
| 6,503,718 B2 | 1/2003 | Shuber et al. |
| 6,586,177 B1 | 7/2003 | Shuber |
| 6,613,580 B1 | 9/2003 | Chow et al. |
| 6,654,505 B2 | 11/2003 | Bridgham et al. |
| 6,670,133 B2 | 12/2003 | Knapp et al. |
| 6,787,308 B2 | 9/2004 | Balasubramanian et al. |
| 6,849,411 B2 | 2/2005 | Knapp et al. |
| 6,960,437 B2 | 11/2005 | Enzelberger et al. |
| 6,969,488 B2 | 11/2005 | Bridgham et al. |
| 7,081,339 B2 | 7/2006 | Slepnev |
| 7,115,400 B1 | 10/2006 | Adessi et al. |
| 7,232,656 B2 | 6/2007 | Balasubramanian et al. |
| 7,238,323 B2 | 7/2007 | Knapp et al. |
| 7,282,370 B2 | 10/2007 | Bridgham et al. |
| 7,459,271 B2 | 12/2008 | Siemering |
| 2001/0041357 A1 * | 11/2001 | Fouillet et al. .............. 435/91.1 |
| 2003/0054372 A1 | 3/2003 | Jaeger |
| 2004/0132034 A1 | 7/2004 | Siemering |
| 2005/0069904 A1 | 3/2005 | Pierson et al. |
| 2008/0286795 A1 | 11/2008 | Kawashima et al. |
| 2010/0111768 A1 | 5/2010 | Banerjee et al. |

FOREIGN PATENT DOCUMENTS

| | | |
|---|---|---|
| WO | 96/02672 A1 | 2/1996 |
| WO | 96/03206 A1 | 2/1996 |
| WO | 96/30934 A1 | 10/1996 |
| WO | 1996/30393 A1 | 10/1996 |
| WO | 97/02357 A1 | 1/1997 |
| WO | 98/00231 A1 | 1/1998 |
| WO | 01/90415 A2 | 11/2001 |

OTHER PUBLICATIONS

Curcio et al. (Continuous Segmented-Flow Polymerase Chain Reaction for High-Throughput Miniaturized DNA Amplification, Anal. Chem., 2003, 75 (1), pp. 1-7, Publication Date (Web): Nov. 28, 2002).*

Kobayashi et al. (Silicon Array of Elongated Through-Holes for Monodisperse Emulsion Droplets, AIChE Journal, vol. 48, Issue 8, pp. 1639-1644, Aug. 2002).*

Fredricks et al. (Application of Polymerase Chain Reaction to the Diagnosis of Infectious Diseases, Clin Infect Dis. Sep. 1999;29(3):475-86; quiz 487-8).*

Nakano et al. (High Speed Polymerase Chain Reaction in Constant Flow, Biosci Biotechnol Biochem. Feb. 1994;58(2):349-52).*

Kopp et al. (Chemical Amplification: Continuous-Flow PCR on a Chip, Science. May 15, 1998;280(5366)1046-8).*

Obeid et al. (Microfabricated Device for DNA and RNA Amplification by Continuous-Flow Polymerase Chain Reaction and Reverse Transcription-Polymerase Chain Reaction with Cycle Number Selection, Anal Chem. Jan. 15, 2003;75(2):288-95).*

Ghadessy et al. (Directed evolution of polymerase function by compartmentalized self-replication, PNAS, Apr. 10, 2001, vol. 98 No. 8, 4552-4557).*

Nisisako et al. (Formation of Droplets Using Branch Channels in a Microfluidic Circuit, SICE 2002. Proceedings of the 41st SICE Annual Conference (vol. 2 ), Aug. 5-7, 2002, 957-959).*

Tawfik et al. (Man-made cell-like compartments for molecular evolution, Nat Biotechnol. Jul. 1998;16(7):652-6).*

Dower et al. (In vitro selection as a powerful tool for the applied evolution of proteins and peptides, Curr Opin Chem Biol. Jun. 2002;6(3):390-8).*

Katsura et al. (Indirect micromanipulation of single molecules in water-in-oil emulsion, Electrophoresis. Jan. 2001;22(2):289-93).*

Lagally et al. (Single-molecule DNA amplification and analysis in an integrated microfluidic device, Anal Chem. Feb. 1, 2001;73(3):565-70).*

Barinaga, Science, vol. 253, pp. 1489 (1991).

Bousse et al., "Electrokinetically Controlled Microfluidic Analysis Systems," Annual Review of Biophysics and Biomolecular Structure, Annual Reviews, Inc., Palo Alto, US (2000), vol. 29, pp. 155-181.

(56) References Cited

OTHER PUBLICATIONS

He et al., "Capillary-based fully integrated and automated system for nanoliter polymerase chain reaction analysis directly from cheek cells", J. Chromatography A., 924, 271-284, (2001).

Karger et al Multiwavelength fluorescence detection for DNA seq. using Capillary Electrophoresis, NAR, vol. 19, pp. 4955-4962 (1991).

Kopp et al., "Chemical Amplification: Continuous Flow PCR on a Chip," Science, American Association for the Advancement of Science (1998), vol. 280, pp. 1046-1048.

Lagally et al., "Single-Molecule DNA Amplification and Analysis in an Integrated Microfluidic Device," Anal. Chem., American Chemical Society, Columbus, US (2001), vol. 73, No. 3, pp. 565-570.

Li et al., (1988) "Amplification and analysis of DNA sequences in single human sperm and diploid cells", Nature, vol. 335 pp. 414-417.

Li et al., "Quantitative polymerase chain reaction using capillary electrophoresis with laser-induced fluorescence detection: Analysis of duck hepatitis B", Anal. Bioanal. Chem., vol. 374, pp. 269-273, (2002).

Matthews et al. Review. Analytical Strategies for the Use of DNA Probes. Analytical Biochemistry 169, pp. 1-25, (1988).

Mitra et al., (2003) "Digital genotyping and haplotyping with polymerase colonies", PNAS, vol. 100, No. 10, pp. 5926-5931.

Mullis et al (1986) "Specific Enzymatic Amplification of DNA in Vitro: The Polymerase Chain Reaction" Cold Spring Harbor Symposia on Quantitave Biology, vol. (LI) 51, pp. 263-273.

Powell, S.J. in PCR Essential Data Protocol Optimization and reaction specificity Essential Data Series, pp. 73-87, (1995).

Prober et al Science vol. 238, (1987), pp. 336-341.

Rawadi et al, "application of an arbitrarily primed polymerase chain reaction to mycoplasma identification and typing within the Mycoplasma mycoides cluster", J. Of Appl. Bact., vol. 78, No. 6, pp. 586-592 1995.

Rungpragayphan S et al, "High-Throughput, Cloning-Independent Protein Library Construction by Combining Single-Molecule DNA Amplification with in Vitro Expression", Journal of Molecular Biology, (2002) 318, pp. 395-405.

Saiki et al (1988). "Primer-Directed Enzymatic Amplification of DNA with a Thermostable DNA Polymerase", Science 239, pp. 487-491.

Service (1998). "Microchips Arrays Put DNA on the Spot", Science, 282, Issue 5388, pp. 396-399.

Skowasch et al "Optimized amplification of polymorphic system", Int. J. of Legal medicine, vol. 105, No. 3, pp. 185-187, (1992).

Thomas et al, "An improved strategy for generating a family of unidirectional deletions on large DNA fragments Gene", Anal. Tech., vol. 7 (4), pp. 87-90, (1990).

Wang et al, (2000). Voltammetry on Microfluidic Chip Platforms; Anal. Chem., 72, pp. 5285-5289.

Wiesner, "Direct quantification of picomolar concentrations of mRNAs by mathematical analysis of a reverse transcription/exponential polymerase chain reaction assay", Nucleic Acids Research, vol. 20, No. 21, pp. 5863-5864, (1992).

Wiesner et al., "Counting Target Molecules by Exponential Polymerase Chain Reaction: Copy Number of Mitochondrial DNA in Rat Tissues", Biochemical and Biophysical Research Communications, vol. 183, No. 2, pp. 553-559 (1992).

Zazzi et al., "Nested Polymerase Chain Reaction for the Detection of Human Immunodeficiency Virus Type 1 DNA in Clinical Specimens," Journal of Medical V, vol. 38, pp. 172-174, (1992).

Zhang et al., (1992) "Whole genome amplification from a single cell: Implications for genetic analysis", Proc. Natl. Acad. Sci. USA, vol. 89, pp. 5847-5851.

Zhang et al., (1999) "Automated and Integrated System for High-Throughput DNA Genotyping Directly from Blood", Anal. Chem., vol. 71, pp. 138-1145.

Zimmerman et al, Methods in Mol. And Cellular Bio vol. 3 pp. 39-42 (1992).

International Search Report, issued in related international application No. PCT/US2003/040599, dated Aug. 19, 2004.

International Search Report, issued in related international application No. PCT/US2005/017065, dated Nov. 3, 2005.

International Preliminary Report on Patentability and Written Opinion, issued in related international application No. PCT/US2005/017065, dated Nov. 3, 2005.

\* cited by examiner

METHODS OF DETECTING LOW COPY NUCLEIC ACIDS

CROSS REFERENCE TO RELATED APPLICATIONS

This application is a divisional of and claims the benefit of pending U.S. patent application Ser. No. 11/873,753, filed Oct. 17, 2007, which is a continuation of U.S. patent application Ser. No. 10/741,162, filed Dec. 19, 2003, which claims priority to and the benefit of Provisional Patent Application U.S. Ser. No. 60/462,384 entitled "Single Molecule Amplification and Detection of DNA in a Microfluidic Format" by Knapp, et al., filed Apr. 11, 2003, and Provisional Patent Application U.S. Ser. No. 60/436,098 entitled "Single Molecule Amplification and Detection of DNA in a Microfluidic Format" by Knapp, et al., filed Dec. 20, 2002, all of which are hereby incorporated herein by reference in their entirety for all purposes.

STATEMENT AS TO RIGHTS TO INVENTIONS MADE UNDER FEDERALLY SPONSORED RESEARCH AND DEVELOPMENT

Part of the technology for this application was developed under NIST-ATP grant 70NANB8H4000. The Government may have certain rights in this invention.

FIELD OF THE INVENTION

The invention is in the field of single molecule detection, e.g., by amplification of single molecules from complex mixtures, e.g., for disease diagnosis, detection of pathogens, environmental contaminants, or the like. Amplifications are conducted in high throughput systems, e.g., microfluidic systems, to provide an ability to detect rare molecules in complex samples that are aliquotted into low copy number reaction mixtures, whereby a rare copy nucleic acid of interest is detected, e.g., by amplifying large numbers of aliquots of the complex samples.

BACKGROUND OF THE INVENTION

The detection of nucleic acids is central to medicine, forensic science, industrial processing, crop and animal breeding and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques.

One of the most powerful and basic technologies for nucleic acid detection is nucleic acid amplification. That is, in many typical formats, such as the polymerase chain reaction (PCR), reverse-transcriptase PCR(RT-PCR), ligase chain reaction (LCR), and Q-β replicase and other RNA/transcription mediated techniques (e.g., NASBA), amplification of a nucleic acid of interest precedes detection of the nucleic acid of interest, because it is easier to detect many copies of a nucleic acid than it is to detect a single copy.

PCR, RT-PCR and LCR are in particularly broad use, in many different fields. Details regarding the use of these and other amplification methods can be found in any of a variety of standard texts, including, e.g.,: Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel") and *PCR Protocols A Guide to Methods and Applications* (Innis et al. eds) Academic Press Inc. San Diego, Calif. (1990) (Innis) Many available biology texts have extended discussions regarding PCR and related amplification methods.

More recently, a number of high throughput approaches to performing PCR and other amplification reactions have been developed, e.g., involving amplification reactions in microfluidic devices, as well as methods for detecting and analyzing amplified nucleic acids in or on the devices. Details regarding such technology is found in the technical and patent literature, e.g., Kopp et al. (1998) "Chemical Amplification: Continuous Flow PCR on a Chip" *Science*, 280 (5366):1046; U.S. Pat. No. 6,444,461 to Knapp, et al. (Sep. 3, 2002) MICROFLUIDIC DEVICES AND METHODS FOR SEPARATION; U.S. Pat. No. 6,406,893 to Knapp, et al. (Jun. 18, 2002) MICROFLUIDIC METHODS FOR NON-THERMAL NUCLEIC ACID MANIPULATIONS; U.S. Pat. No. 6,391,622 to Knapp, et al. (May 21, 2002) CLOSED-LOOP BIOCHEMICAL ANALYZERS; U.S. Pat. No. 6,303,343 to Kopf-Sill (Oct. 16, 2001) INEFFICIENT FAST PCR; U.S. Pat. No. 6,171,850 to Nagle, et al. (Jan. 9, 2001) INTEGRATED DEVICES AND SYSTEMS FOR PERFORMING TEMPERATURE CONTROLLED REACTIONS AND ANALYSES; U.S. Pat. No. 5,939,291 to Loewy, et al. (Aug. 17, 1999) MICROFLUIDIC METHOD FOR NUCLEIC ACID AMPLIFICATION; U.S. Pat. No. 5,955,029 to Wilding, et al. (Sep. 21, 1999) MESOSCALE POLYNUCLEOTIDE AMPLIFICATION DEVICE AND METHOD; U.S. Pat. No. 5,965,410 to Chow, et al. (Oct. 12, 1999) ELECTRICAL CURRENT FOR CONTROLLING FLUID PARAMETERS IN MICROCHANNELS, and many others.

Despite the wide-spread use of amplification technologies and the adaptation of these technologies to truly high throughput systems, certain technical difficulties persist in amplifying and detecting nucleic acids, particularly rare copy nucleic acids. This is particularly true where the amplification reagents amplify a high copy nucleic acid in a given sample in addition to the rare nucleic acid and the two nucleic acids differ by only one or a few nucleotides in the same sample. For example, if a set of primers hybridizes to a high copy nucleic acid, as well as to a low copy nucleic acid in a given sample, the geometric amplification of the high copy nucleic acid proportionately dominates the amplification reaction and it is difficult or impossible to identify the low copy nucleic acid in any resulting population of amplified nucleic acids. Thus, low copy number alleles of a gene can be very difficult to detect, e.g., where a primer set cannot easily be identified that only amplifies the rare nucleic acid (and the practitioner will realize that perfect reagent specificity is rare or non-existent in practice). Amplification of the higher copy number nucleic acids in the sample swamps out any signal from the low copy nucleic acid. In spite of such difficulties, identification of rare copy nucleic acids can be critical to identifying disease or infection in the early stages, as well as in many other applications.

It is worth noting that these problems simply have not been addressed by the prior art. While a few authors have described single copy amplification as a theoretical exercise (e.g., Mullis et al (1986) *Cold Spring Harbor Symp. Quant. Biol.* 51:263-273; Li et al. (1988) *Nature* 335:414-417; Saiki et al (1988) *Science* 239:487-491, and Zhang et al (1992) *Proc. Natl. Acad. Sci. USA* 89:5847-5851), and others have described stochastic PCR amplification of single DNA template molecules followed by CE analysis of products in a microscale device (Lagally et al. (2001) *Anal. Chem.* 73:565-570), none of these prior approaches are suitable for detection of rare copy nucleic acids in samples. That is, none of these approaches are suitable for high throughput automation and the devices in the prior art cannot be adapted to practicably detect rare copy nucleic acids. For example, the device of Lagally et al., id., flowed sample to be amplified into chambers, stopped flow of the system, ran the amplification reaction, manually reconfigured the device to flow amplification products out of the chambers, ran the amplification products out of the chambers for one reaction at a time, and detected the product. This cumbersome process results in few amplification reactions being made and analyzed in any useful time period and required almost continuous user intervention to make the system operate.

Another difficulty with amplification methods that is completely unaddressed in the prior art is that it can be quite difficult to perform quantitative analysis on rare nucleic acids. The problems noted above for detection apply to quantitative analysis as well, with the additional problem that quantification is impacted by the presence of high copy number nucleic acids in the sample, even if the rare nucleic acid can be amplified. This is because, even if the amplification is sufficiently specific that detection of the rare nucleic acid can occur, the high copy number nucleic acids still have competitive effects on the amplification reaction, in that they compete with the rare nucleic acid for reaction components during the amplification reaction. Thus, it is not generally possible to assess accurately the concentration of rare nucleic acids in a sample, particularly where the components of the system have not previously been characterized (it is, of course, somewhat simpler to assess amplification products quantitatively if the materials selected for amplification are already characterized). While amplification of materials that have already been fully characterized is of academic interest, this approach is of little practical value if it cannot be adapted to characterization of unknown materials. For example, the inability to quantify rare nucleic acids limits, e.g., the ability to diagnose disease, to establish disease prognosis and to perform accurate statistical assessments of the nucleic acid of interest.

The subject invention overcomes these difficulties by providing robust high throughput methods of identifying and quantifying rare nucleic acids of interest in a sample. A number of related methods and systems for identifying and quantifying rare nucleic acids of interest in the sample are provided herein.

SUMMARY OF THE INVENTION

The present invention relates to the surprising discovery that single molecule amplification can be used for the detection and statistical characterization of rare nucleic acids of interest in a sample, e.g., for disease diagnosis (e.g., cancer diagnosis), detection of pathogens, detection of rare environmental nucleic acids, and the like. For example, many individual amplification reactions can be performed on reaction mixtures derived from a sample comprising a rare nucleic acid of interest, where each reaction mixture has few (e.g., 1) or no copies of the rare a nucleic acid of interest, e.g., until the nucleic acid of interest is identified in a reaction mixture. Additional nucleic acids in the sample can also be amplified in low copy number reactions and statistical methods can be used to determine the relative ratio of the nucleic acid of interest to the additional nucleic acid, e.g., to determine relative or absolute concentration of the nucleic acid of interest. Desirably, most or all of the steps in the methods herein can be performed in a continuous flow format to greatly speed the rate of the overall method. Alternately, one or more of the steps can be performed in a stopped flow mode, e.g., where the detector is configured to simultaneously scan multiple amplification regions at once (simultaneous detection provides for increased throughput in these embodiments).

High throughput amplification systems such as those embodied in high throughput microfluidic systems are particularly well adapted to performing these methods, which can be used to detect nucleic acids of interest that are present at exceedingly low concentrations in a sample to be analyzed, e.g., by performing many low copy number amplification reactions until the nucleic acid of interest is detected, and/or until enough copies of the nucleic acid of interest are detected that reliable statistical evaluations can be performed. In a related aspect, the invention also provides new ways of determining whether and how many copies of an initial nucleic acid are present in a reaction mixture (or whether the initial nucleic acid is present in a reaction mixture) by considering how much a signal from the initial nucleic acid disperses during amplification and comparing the dispersion to expected dispersion arising from thermal diffusivity and/or Taylor Aris dispersion, or related phenomena (or even simply by comparison of the observed dispersion to empirically observed control reactions). This can include monitoring the shape (amplitude, signal width, and/or other signal shape features) of a signal generated from an aliquot comprising the nucleic acid of interest to a predicted or empirically observed signal shape. These shape features of the signal are extremely reproducible, which provides an ability to distinguish signals of interest from background random signal fluctuations. Both the number of molecules in an aliquot and the ability to distinguish signals of interest from background signal fluctuations can be performed by this class of methods. Systems and kits adapted to performing the various methods herein are also a feature of the invention. The nucleic acids that are quantified can be known (e.g., controls) or unknown in composition. They can include experimental nucleic acids (the nucleic acids of primary interest in the experiment at issue) or can be other unknown nucleic acids (e.g., uncharacterized genomic and/or cDNA from a biological sample of interest).

Accordingly, in a first aspect, methods of detecting a nucleic acid of interest are provided. In the methods, a sample comprising the nucleic acid of interest and one or more additional nucleic acid is aliquotted into a plurality of reaction mixtures. At least two of the reaction mixtures are single copy reaction mixtures, each comprising a single copy of the nucleic acid of interest. The plurality of reaction mixtures additionally comprise at least one additional reaction mixture comprising at least one copy of the additional nucleic acid. The plurality of reaction mixtures are subjected to one or more amplification reaction (in this context, the amplification reaction may or may not amplify the nucleic acid of interest, i.e., if the reaction has zero copies of the nucleic acid of interest, it will not be amplified; if it has one or more copy it will). The nucleic acid of interest is detected in one or more of the single copy reaction mixtures.

In a closely related aspect, the invention includes methods of detecting a low copy nucleic acid of interest in a sample that has one or more higher copy additional nucleic acid that is different from the low copy nucleic acid. The method includes aliquotting the sample into a plurality of reaction mixtures. The mixtures include a plurality (e.g., about 5, or more, about 10 or more, about 50 or more, about 100 or more, about 150 or more, or about 500 or more) of zero copy reaction mixtures that include zero copies of the nucleic acid of interest and at least one single copy reaction mixture comprising a single copy of the nucleic acid of interest. The zero and single copy reaction mixtures are subjected to an amplification reaction (whether an amplification actually occurs or not). The nucleic acid of interest is then detected in the single copy reaction mixture (this includes the possibility that the nucleic acid of interest is detected in one or in multiple individual single copy reactions).

In an additional related class of embodiments, related methods of quantifying a nucleic acid of interest in a sample are provided. In the methods, the sample is aliquotted into at least 25 reaction mixtures comprising 2 or fewer copies of the nucleic acid of interest each (and generally 1 or fewer). The reaction mixtures are subjected to one or more amplification reactions. The nucleic acid of interest is then detected in a plurality of the reaction mixtures. In a number of embodiments, statistical evaluations of the nucleic acid of interest are performed based upon the detection of the nucleic acid of interest in the plurality of reaction mixtures. In one class of embodiments, at least 50 or more, at least 75 or more, or at least 100 or more reaction mixtures, comprising the 2 or fewer copies, are subjected to the one or more amplification reactions.

In an additional class of related embodiments, methods of detecting a low copy nucleic acid of interest are provided. In the methods, a sample comprising the low copy nucleic acid of interest is aliquotted into a plurality of reaction mixtures. A plurality of the reaction mixtures contain zero copies of the nucleic acid of interest and at least one of the reaction mixtures comprises at least one copy of the nucleic acid of interest. A plurality of the plurality of zero copy reaction mixtures is subjected to one or more amplification reaction in a microfluidic device comprising at least one microchamber or microchannel. The nucleic acid of interest is determined not to be present in the zero copy reaction mixtures. At least one additional zero copy reaction mixture and the reaction mixture comprising the nucleic acid of interest are subjected to one or more amplification reaction. The nucleic acid of interest is detected in the reaction mixture comprising the nucleic acid of interest. Put another way, the reaction mixtures are amplified and checked for the presence of the nucleic acid of interest in the microfluidic device, at least until the nucleic acid is detected. For a low copy number nucleic acid, this can require a large number of amplification reactions be performed on the zero copy reaction mixtures until the nucleic acid of interest is found.

The invention also provides methods for quantifying a nucleic acid of interest in a sample, e.g., by taking diffusion/dispersion into consideration. In the methods, a sample comprising a copy of the nucleic acid of interest, or a complement thereof, is aliquotted into at least one reaction mixture. The reaction mixture is subjected to at least one amplification reaction, thereby amplifying the copy of the nucleic acid of interest. A shape, volume, width, length, height, area, or the like, in which the nucleic acid of interest, or a signal corresponding thereto, is present is detected. The shape, volume, width, height, length, or area is correlated to a number of copies of the nucleic acid of interest in the reaction mixture or sample, thereby quantifying the nucleic acid of interest in the sample. Because these shape features of the signal are extremely reproducible, it is straightforward to distinguish signals of interest from background random signal fluctuations. In a related aspect, knowledge of diffusion/dispersion and the reproducibility of these phenomena can be used to reliably distinguish the signal of a one or more target molecule(s) from random baseline system fluctuations. In any case, this correlation can be performed in any of a variety of ways, e.g., by comparing the shape, volume, width, height, length and/or other signal shape features to predicted values taking thermal diffusivity and/or Taylor-Aris dispersion into account and/or by back calculation from empirically observed values for known reactions performed in the system. It is worth noting that this method is particularly relevant to continuous flow systems, where materials disperse during flow.

In yet another class of embodiments, high throughput stopped flow methods of detecting rare nucleic acids are provided. For example, methods of detecting a nucleic acid of interest are provided, in which a sample comprising the nucleic acid of interest is aliquotted into a plurality of reaction mixtures. At least two of the reaction mixtures are single copy reaction mixtures, each comprising a single copy of the nucleic acid of interest. The reaction mixtures are flowed throughout a network of microchannels and subjected to one or more amplification reaction under stopped flow conditions in the network of microchannels. The nucleic acid of interest is detected in the single copy reaction mixtures under the stopped flow conditions. Desirably, the detection step can include detection of multiple reaction products simultaneously. For example, a CCD array or appropriate image processor can be used to scan an entire chip (or sub-regions thereof) for "clouds" of signal from amplified products. That is, an entire channel or network of channels can be scanned simultaneously after amplification and any or all regions where signal arising from amplification can be detected simultaneously (or in more than one pass of the scanner/detector, if desired).

It will be appreciated that the above methods overlap with one another and that any of the above methods can be performed in combination with one another. Similarly, any or all of the above methods can be practiced in a continuous flow format to improve throughput of the relevant method, and/or can use stopped flow in combination with image analysis of multiple regions of (or an entire) microchannel network.

For any or all of the methods herein, the reaction mixture can comprise the nucleic acid of interest and one or a plurality of additional nucleic acids, with the relevant method including detecting the nucleic acid of interest and/or the plurality of additional nucleic acids in the reaction mixture. The methods optionally include adding up the number of nucleic acids of interest, or the plurality of additional nucleic acids, or both, in the reaction mixture or the sample, or both. A ratio of the nucleic acid of interest or the plurality of additional nucleic acids in the reaction mixture to the sum of the nucleic acid of interest and/or the plurality of additional nucleic acids in the reaction mixture or sample can be determined. From this, a concentration of the nucleic acid of interest in the reaction mixture or sample can be determined. Similarly, the sum of the number of nucleic acids of interest and the plurality of additional nucleic acids can provide an indication of the total number of nucleic acids in the reaction mixture.

For any or all of the methods herein, aliquotting the sample or reaction mixture can comprise diluting the sample into a plurality of reaction containers (e.g., wells in a microtiter plate), and/or flowing the sample into a microfluidic dilution channel or chamber. In microfluidic embodiments, the sample is optionally diluted in the microfluidic dilution channel or chamber, whereby the sample is aliquotted into multiple diluted aliquots in the microfluidic dilution channel or chamber. Optionally, the part or all of the aliquotting/dilution process can be multiplexed, e.g., by flowing a plurality of samples into the device or reaction containers simultaneously. Samples, aliquots, reaction mixtures, etc., can be flowed under pressure (e.g., into the microfluidic device) or via electroosmosis, or by any other available method. For convenience in microfluidic embodiments, the sample can be diluted from a common reaction component reservoir, e.g., comprising some or all of the reaction and/or buffer components for the amplification reactions (e.g., polymerase, primers, locus specific reagents, labels, salts, magnesium, water and/or the like). Alternately, one or more component can be located in one or more additional reservoir and the components can be mixed prior to amplification. Desirably, any or all of these steps can be practiced in a continuous flow format, or utilizing the stopped flow/simultaneous image analysis methods noted herein.

The concentration of the nucleic acids of interest and/or any additional nucleic acid is optionally low in the methods of the invention, e.g., about 1 molecule per aliquot. For example, the sample can be diluted to a concentration of about 1 molecule of interest per nanoliter or less. Optionally, diluted aliquots are each diluted to the same degree; however, diluted aliquots can also be differentially diluted (e.g., to form a dilution series). The shape, volume of the aliquots can be quite low to keep reagent costs low, e.g., in microfluidic applications. For example, the aliquots can be less than about 100 nl in volume, e.g., less than about 10 nl in volume, or, e.g., about 1 nl in volume or less.

In a number of embodiments, at least one of the reaction mixtures is in an aqueous solution (the enzymes used in typical amplification reactions typically function well in an aqueous environment). This can take the form of sample plugs in a microfluidic device, fluid in reservoirs of a microtiter plate, or other forms such as where at least one of the reaction mixtures is formulated in an aqueous phase of an emulsion comprising aqueous droplets suspended in an immiscible liquid (in this embodiment, amplification can be performed on the reaction mixture when it is formulated in the emulsion). In the emulsion embodiment, the nucleic acid of interest is optionally present as a single copy in at least one aqueous droplet of the aqueous phase prior to performing the amplification reaction. The nucleic acid of interest is detected in the emulsion after the amplification reaction is performed. Optionally, a plurality of additional nucleic acids are also formulated in the aqueous phase of the emulsion and the method comprises detecting the plurality of additional nucleic acids. As with other embodiments herein, statistical analysis can be performed on, e.g., the ratio of the additional nucleic acids in the emulsion to the nucleic acid of interest, e.g., to determine the concentration of the nucleic acids of interest in the emulsion.

In any of the methods herein, at least 10 of the reaction mixtures are optionally low copy reaction mixtures (e.g., comprising 100 or fewer, usually 50 or fewer, typically 10 or fewer, generally 2 or fewer and often 1 or fewer copies of the nucleic acid of interest or the additional nucleic acid). Optionally, at least 25, at least 50, at least 100, at least 150, at least 500 or more of the reaction mixtures are low copy reaction mixtures. The low copy reaction mixtures can comprise at least 10, at least 25, at least 50, at least 100, at least 150 at least 500 or more single or zero copy reaction mixtures comprising 1 or fewer copies of the nucleic acid of interest. The reaction mixtures can, and often do, comprise no copies of the nucleic acid of interest. Thus, a plurality of the reaction mixtures can comprise a plurality of zero copy reaction mixtures that comprise no copies of the nucleic acid of interest. That is, at least about 10, 25, 50, 100, 150, 500, 1,000 or even 10,000 or more of the reaction mixtures can be zero copy reaction mixtures that have no copies of the nucleic acid of interest. In one aspect, the invention provides the ability to rapidly search through many such zero copy reaction mixtures to identify a nucleic acid of interest.

In several embodiments of the invention, the sample comprises at least one additional nucleic acid that is different than the nucleic acid of interest. The additional nucleic acid can, and often does, exist at a higher copy number in the sample than the nucleic acid of interest. The additional nucleic acid can be a known nucleic acid (e.g., a control or hybridization blocking nucleic acid) or can itself be unknown with respect to part or all of the composition (a common occurrence where the nucleic acid of interest is to be detected in a biological sample, e.g., a cell or tissue sample from a patient. For example, the additional nucleic acid can be present at a concentration at least about 100×, at least about 1,000×, at least about 10,000×, at least about 100,000×, at least about 1,000,000× or greater as high as the nucleic acid of interest in the sample (that is, can have at least about 100×, at least about 1,000×, at least about 10,000×, at least about 100,000×, at least about 1,000,000× or greater as many copies as the nucleic acid of interest in the sample). By screening sufficient numbers of sample aliquots, the nucleic acid of interest can be detected regardless of its relative concentration.

Optionally, the additional nucleic acid can be detected independent of the nucleic acid of interest. A ratio of the nucleic acid of interest to the additional nucleic acid can be determined, e.g., for statistical analysis of the nucleic acid of interest and/or the additional nucleic acid. The number of nucleic acids in the reaction mixture (whether the nucleic acid(s) of interest, the additional nucleic acids or other nucleic acids) can be added up and the concentration of the nucleic acids (or the relative concentrations) can be determined in the sample, or in any of the various aliquots and reaction mixtures herein.

The nucleic acid of interest can be essentially any detectable nucleic acid. Examples include SNPs, low copy nucleic acids, cancer associated nucleic acids, infective or pathogen associated nucleic acids, forensic nucleic acids, and the like. Because of the ability of the methods of the invention to identify extremely low copy number nucleic acids, the invention is suitably applied to early stage disease diagnosis where cancer cells or pathogens are present at low concentrations. For example, colon cancer cells can be present in stool samples, but, at least in the early stages of colon cancer, the concentration of cancer cell DNA is small compared to the overall DNA in such a sample (typically much less than 1% of the cells from which the DNA sample was derived). The present invention can be used to identify and quantify cancer DNA in such a sample, providing a new method for disease diagnosis and prognostication. Similar approaches can be used to identify cancerous DNAs or pathogen nucleic acids from any fluid or tissue from which such samples are normally taken or derived, e.g., blood, urine, saliva, tears, sputum, stool, ejaculatory fluid, vaginal secretions, or the like. From these samples, infective/pathogenic agents such as viruses (e.g., HIV, herpes virus, pox virus, etc.), parasites (e.g., malarial parasites (*Plasmodium*), nematodes, etc.), bacteria (e.g., pathogenic *E. coli, salmonella*, etc.) can be identified. Where the pathogen is present at a relatively low concentration relative to related non-pathogenic organisms (e.g., pathogenic *E. coli* are present at an initially low concentration in the gut, as compared to non-pathogenic *E. coli*), the methods are particularly suitable.

Most typically, the methods of the invention utilize thermocyclic amplification reactions, although non-thermocyclic reactions (e.g., using denaturants in place of heat, a procedure that is relatively practical in microscale applications) can also be used. In one typical class of embodiments, the reaction mixtures are subjected to one or more amplification reaction(s) by thermocycling the reaction mixtures in one or more microscale amplification chamber or channel. A variety of thermocycling methods can be used in a microscale device (or in reaction containers), e.g., heating by applying electrical current to fluid of the reaction mixture (e.g., in the microscale amplification chambers or channels), resistively heating a heating element that contacts or is in proximity to the reaction mixture (e.g., in the microscale amplification chambers or channels), heating with a Joule-Thompson or Peltier device, or any other available heating or heating and cooling method(s).

Optionally, the components of the system can be treated with one or more reagent between operational runs to reduce cross contamination between operations. For example, the amplification channel can have acid or base flowed into the channel between amplification reactions to reduce unwanted contamination from one or more previous amplification products.

In a convenient class of embodiments, detecting can include real time PCR detection, e.g., via use of TaqMan™ probes (operating by detecting a double-labeled probe before, during, or after polymerase-mediated digestion of the double labeled probe), use of molecular beacons, or the like. Real time detection can be omitted, e.g., simply by detecting amplicons via labeled probes, e.g., after separation of the amplicon from unlabeled probe.

Optionally, the detecting step(s) can include quantifying the nucleic acid of interest in the reaction mixtures, or the sample, or both. Alternately, the nucleic acid can be quantified separate from the detection step. In either case, quantifying the nucleic acid of interest optionally comprises detecting the nucleic acid in a plurality of single-copy reaction mixtures and performing statistical or probabilistic analysis to determine a percentage or distribution of reaction mixtures comprising a single copy of the nucleic acid of interest. The statistical or probabilistic analysis can comprise any available technique or combination thereof, e.g., Poisson analysis, Monte Carlo analysis, application of a genetic algorithm, neural network training, Markov modeling, hidden Markov modeling, multidimensional scaling, partial least squares (PLS) analysis, or principle component analysis (PCA).

In any of the methods, the initial starting concentration of a nucleic acid of interest can be determined, e.g., by detecting a reproducible shape, length, width, height, volume or area of signal for the nucleic acid of interest in a given reaction mixture. For example, the signal can be detected from a label bound to the nucleic acid of interest. The shape, length, width, height, volume or area is optionally correlated to a number of nucleic acids interest present in one of the reaction mixtures, and/or present in the sample based upon a Taylor-Aris dispersion calculation, or a thermal diffusivity calculation, or both, or by comparison to an empirically observed set of reaction mixtures having a known number of starting nucleic acids for amplification. Thus, in one aspect, the invention comprises calculating diffusion, or dispersion, or both, of one or more amplified nucleic acids in the given reaction mixture, and correlating the diffusion, or the dispersion, or both, to a number of copies of the nucleic acid of interest in one of the given reaction mixtures prior to amplification.

Systems and/or kits adapted for practicing the methods herein are a feature of the invention. The systems and/or kits can include system instructions (e.g., embodied in a computer or in a computer readable medium, e.g., as system software) for practicing any of the method steps herein. Fluid handling elements for aliquotting/diluting samples, e.g., microfluidic handling elements, and detector elements can also be components of the systems and kits herein. In addition, packaging materials, integration elements (e.g., instrument cases, power supplies, etc.), instructions for using the systems and kits and the like can be features of the invention.

In one embodiment, the invention provides a system for detecting low copy nucleic acids of interest in a sample. The system includes a dilution module that dilutes the sample into multiple aliquots and a microfluidic device comprising an amplification channel or chamber configured to thermocycle one or more of the multiple aliquots. A detector integral with or proximal to the microfluidic device is also included, where the detector is configured to detect one or more amplified copies of the nucleic acid of interest in or on the microfluidic device. System instructions that direct the dilution module to aliquot the sample into a plurality of aliquots, including a plurality of zero copy aliquots comprising no copies of the nucleic acids of interest and one or more single copy aliquot comprising a single copy of the nucleic acid of interest are also included. Typically, the system also includes system software that correlates a reproducible signal shape, length, width, volume or area occupied by amplified copies of the nucleic acid of interest, as detected by the detector, to the number of copies of the nucleic acid of interest present in one of the aliquots, or to the number of copies of the nucleic acid of interest present in the sample, or both. Any or all of the system components can be selected to operate such that a sample of interest is continuously flowed during operation of the system. Alternately, the stopped flow/simultaneous image analysis methods noted herein can be applied.

In a related embodiment, systems for quantifying one or more low copy nucleic acid of interest in a sample are provided. In the systems, a dilution module dilutes the sample into multiple aliquots. A microfluidic device comprising an amplification channel or chamber is configured to thermocycle one or more of the multiple aliquots. A detector integral with or proximal to the microfluidic device is configured to detect a reproducible shape, length, width, volume or area occupied by amplified copies of the nucleic acid of interest present in one of the aliquots following thermocycling of the aliquots. The system also includes system software that correlates the shape, length, width, volume or area occupied by amplified copies of the nucleic acid of interest to the number of copies of the nucleic acid of interest present in one of the aliquots, or to the number of copies of the nucleic acid of interest present in the sample, or both. Optionally, the system includes system instructions that direct the dilution module to aliquot the sample into a plurality of aliquots, including a plurality of zero copy aliquots comprising no copies of the nucleic acids of interest and one or more single copy aliquot comprising a single copy of the nucleic acid of interest.

For either of the above system embodiments, the dilution module is optionally integral with the microfluidic device. The microfluidic device also can include one or more electrodes positioned to flow electrical current into the microchamber or channel. Flow of current into the microchamber or channel can be used to heat fluid in the microchamber or channel. The microfluidic device optionally includes or is coupled to one or more heating element (e.g., a resistive heating element, a Peltier device or a Joule Thompson device) positioned within or proximal to the microchamber or channel, which heats fluid in the microchamber or channel.

The detector is typically configured to detect one or more electromagnetic energy signal in or on the microfluidic device, although other in device sensors (e.g., pH, conductivity, etc.) can also be used. For example, the detector can detect fluorescence, luminescence and/or fluorescence polarization of the sample.

The system optionally comprises software with instructions for performing any of the method steps herein. For example, the system can include statistical or probabilistic system software that performs one or more statistical or probabilistic analysis of signals received from one or more of the aliquots subjected to thermocycling. For example, the statistical or probabilistic analysis can include Poisson analysis, Monte Carlo analysis, application of a genetic algorithm, neural network training, Markov modeling, hidden Markov modeling, multidimensional scaling, PLS analysis, and/or PCA analysis. The statistical or probabilistic analysis optionally comprises quantitatively determining a concentration, proportion, or number of the nucleic acids of interest in the sample.

The systems above also optionally includes fluid handling or storage features such as sample storage modules that stores the sample until it is diluted by the dilution module, a sample retrieval module that retrieves the sample from the sample storage module and delivers it to the dilution module, or the like. These features are optionally designed to provide for continuous flow of fluid (e.g., comprising the sample) through the system (thereby providing for higher sample throughput). Alternately, or in combination, stopped flow/simultaneous image analysis can be used in the systems herein.

Any of the above methods or systems can be used in combination. Additional features of the invention will become apparent upon review of the following.

DETAILED DESCRIPTION

Figure 1:
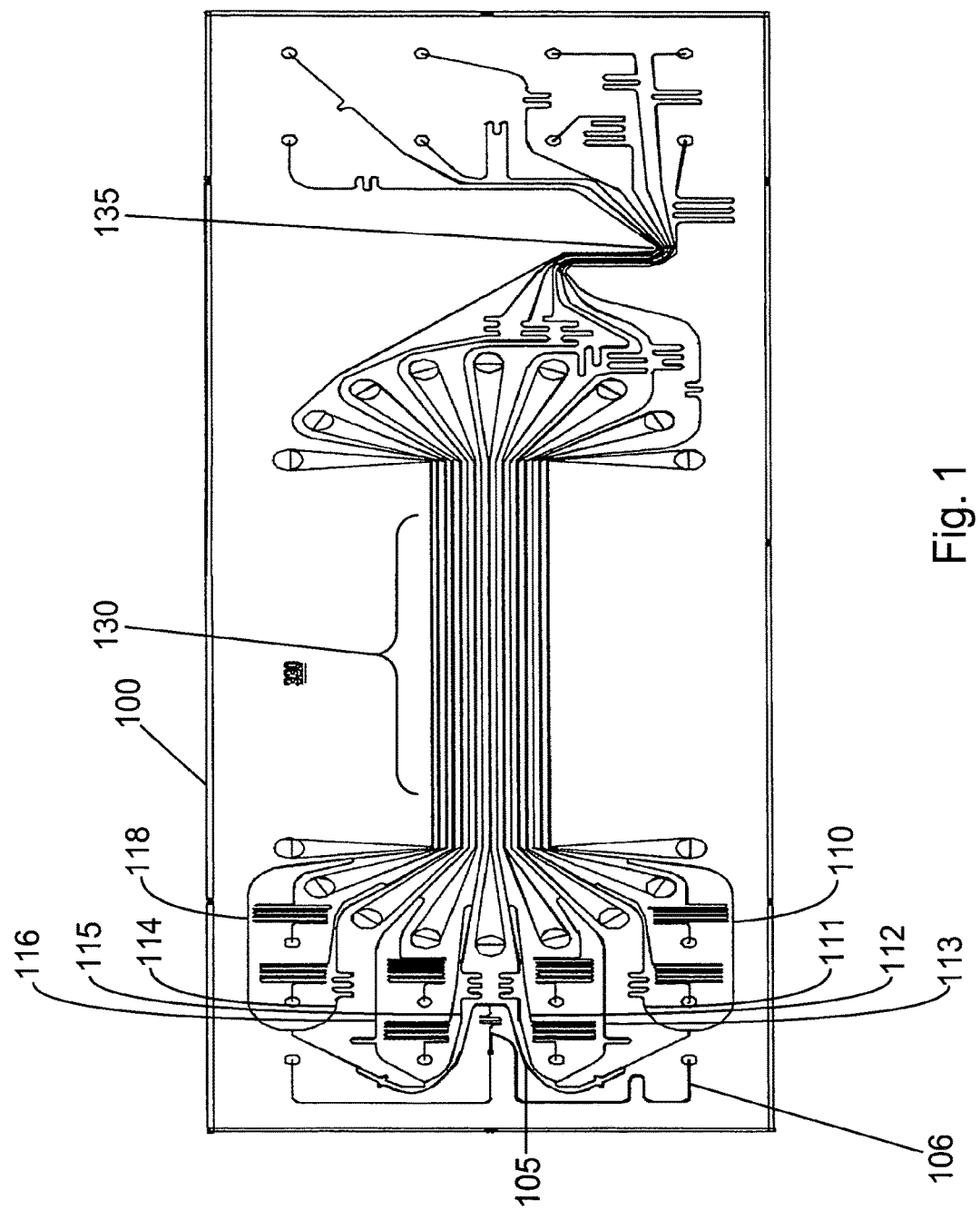
FIG. 1 schematically illustrates a chip design for an 8 channel PCR sipper chip used in the Examples herein.

The present invention derives, in part, from a surprising conceptual shift in considering how rare nucleic acids can be amplified and detected in or from a sample. In the past, detection of rare nucleic acids was performed by trying to find ways of improving the specificity and sensitivity of amplification and detection reactions. This is because the better the reaction can specifically amplify and identify a nucleic acid of interest, the better the reliability and throughput of the system. Considering a simple analogy, when trying to find a needle in a haystack, prior art thinking focuses on more efficient ways of extracting the needle from the haystack.

The present invention takes an entirely different approach to identifying nucleic acids of interest. Instead of trying to fish the nucleic acid of interest out of a complex sample directly, the entire sample is simply deconstructed into low copy number aliquots and the low copy number aliquots are subjected to amplification reactions until the nucleic acid of interest is found. Continuing with the simple analogy, the entire haystack is broken apart into individual pieces of hay and each is examined to see if it is hay or needle.

Modern high-throughput systems make this new conceptual approach possible, i.e., the ability to run massively high numbers of amplification reactions at low cost, e.g., using microfluidic amplification technologies, makes it possible to much more exhaustively sample for any particular nucleic acid of interest in a sample. The continuous flow or high throughput stopped flow nature of these systems further facilitates the approach. Furthermore, examination of a sample by such exhaustive sampling methods provides a great deal of quantitative information (and the concomitant possibility of statistical analysis) with respect to the composition of the sample and the abundance of the nucleic acid of interest. This, in turn, provides diagnostic and prognostic information relevant to the abundance (or relative abundance) of the nucleic acid of interest.

Definitions

It is to be understood that this invention is not limited to particular devices or biological systems, or amplification methods, which can, of course, vary. It is also to be understood that the terminology used herein is for the purpose of describing particular embodiments only, and is not intended to be limiting. As used in this specification and the appended claims, the singular forms "a", "an" and "the" optionally include plural referents unless the content clearly dictates otherwise. Thus, for example, reference to "a microfluidic device" optionally includes a combination of one, two or more devices.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

An "aliquot" is a portion of a component of interest (e.g., a sample). The aliquot can be diluted, concentrated or undiluted as compared to the component of interest.

A "nucleic acid of interest" is any nucleic acid to be amplified, detected and/or quantified in a sample.

An "amplification reaction" is a reaction that 1) results in amplification of a template, or 2) would result in amplification of a template if the template were present. Thus, an "amplification reaction" can be performed on a sample aliquot that comprises a nucleic acid to be amplified, or on a sample aliquot that does not comprise the nucleic acid. Actual amplification of a template is not a requirement for performing an amplification reaction.

A "zero copy" reaction mixture or aliquot is a reaction mixture or aliquot that has no copies of the relevant nucleic acid (e.g., a nucleic acid of interest, or an additional nucleic acid). It can comprise nucleic acids from a sample other than the relevant nucleic acid(s), or it can be completely devoid of any template nucleic acids from the sample.

A "single copy" reaction mixture or aliquot is a reaction mixture or aliquot that has 1 copy of the relevant nucleic acid.

A "low copy" reaction mixture or aliquot is a reaction mixture or aliquot that has only a few copies of the relevant nucleic acid(s). Typically, such a reaction will have 50 or fewer, generally 25 or fewer, usually 10 or fewer and often 5 or fewer, 2 or fewer or 1 or fewer copies of the relevant nucleic acid(s).

A "high copy" nucleic acid reaction mixture or aliquot has at least 1 order of magnitude more copies than the low copy number reaction mixture or aliquot, and generally 2, 3, 4, or even 5 or more orders of magnitude more than the low copy number reaction mixture.

A nucleic acid is "quantified" or "quantitated" in a sample when an absolute or relative number of the nucleic acid in a sample is determined. This may be expressed as a number of copies, a concentration of the nucleic acid, a ratio of the nucleic acid to some other constituent of the sample (e.g., another nucleic acid), or any other appropriate expression.

Nucleic Acids and Samples of Interest

The nucleic acid of interest to be detected in the methods of the invention can be essentially any nucleic acid. The sequences for many nucleic acids and amino acids (from which nucleic acid sequences can be derived via reverse translation) are available. No attempt is made to identify the hundreds of thousands of known nucleic acids, any of which can be detected in the methods of the invention. Common sequence repositories for known nucleic acids include GenBank EMBL, DDBJ and the NCBI. Other repositories can easily be identified by searching the internet. The nucleic acid can be an RNA (e.g., where amplification includes RT-PCR or LCR) or DNA (e.g., where amplification includes PCR or LCR), or an analogue thereof (e.g., for detection of synthetic nucleic acids or analogues thereof). Any variation in a nucleic acid can be detected, e.g., a mutation, a single nucleotide polymorphism (SNP), an allele, an isotype, etc. Further, because the present invention is quantitative, one can detect variation in expression levels or gene copy numbers by the methods.

In general, the methods of the invention are particularly useful in screening samples derived from patients for the nucleic acid of interest, e.g., from bodily fluids and/or waste from the patient. This is because samples derived from relatively large volumes of such materials can be screened in the methods of the invention (removal of such materials is also relatively non-invasive). The nucleic acids of interest (e.g., present in cancer cells) can easily comprise 1% or less of the related nucleic acid population of the sample (e.g., about 1%, 0.1%, 0.001%, 0.0001% or less of the alleles for the gene of interest). Thus, stool, sputum, saliva, blood, lymph, tears, sweat, urine, vaginal secretions, ejaculatory fluid, or the like, can easily be screened for rare nucleic acids by the methods of the invention, as can essentially any tissue of interest. These samples are typically taken, following informed consent, from a patient by standard medical laboratory methods.

Prior to aliquotting and amplification, nucleic acids are optionally purified from the samples by any available method, e.g., those taught in Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and/or *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). A plethora of kits are also commercially available for the purification of nucleic acids from cells or other samples (see, e.g., Easy-Prep™, FlexiPrep™, both from Pharmacia Biotech; StrataClean™, from Stratagene; and, QIAprep™ from Qiagen). Alternately, samples can simply be directly subjected to amplification, e.g., following aliquotting and dilution. One advantage of single molecule detection is that the low concentration of sample components in the reaction can reduce the need for nucleic acid purification. That is, dilution of the sample reduces the abundance of unwanted components at the same time it distributes the nucleic acid of interest into reaction mixtures.

One preferred class of nucleic acids of interest to be detected in the methods herein are those involved in cancer. Any nucleic acid that is associated with cancer can be detected in the methods of the invention, e.g., those that encode over expressed or mutated polypeptide growth factors (e.g., sis), overexpressed or mutated growth factor receptors (e.g., erb-B1), over expressed or mutated signal transduction proteins such as G-proteins (e.g., Ras), or non-receptor tyrosine kinases (e.g., abl), or over expressed or mutated regulatory proteins (e.g., myc, myb, jun, fos, etc.) and/or the like. In general, cancer can often be linked to signal transduction molecules and corresponding oncogene products, e.g., nucleic acids encoding Mos, Ras, Raf, and Met; and transcriptional activators and suppressors, e.g., p53, Tat, Fos, Myc, Jun, Myb, Rel, and/or nuclear receptors. p53, colloquially referred to as the "molecular policeman" of the cell, is of particular relevance, as about 50% of all known cancers can be traced to one or more genetic lesion in p53.

Taking one class of genes that are relevant to cancer as an example for discussion, many nuclear hormone receptors have been described in detail and the mechanisms by which these receptors can be modified to confer oncogenic activity have been worked out. For example, the physiological and molecular basis of thyroid hormone action is reviewed in Yen (2001) "*Physiological and Molecular Basis of Thyroid Hormone Action*" *Physiological Reviews* 81(3):1097-1142, and the references cited therein. Known and well characterized nuclear receptors include those for glucocorticoids (GRs), androgens (ARs), mineralocorticoids (MRs), progestins (PRs), estrogens (ERs), thyroid hormones (TRs), vitamin D (VDRs), retinoids (RARs and RXRs), and the peroxisome proliferator activated receptors (PPARs) that bind eicosanoids. The so called "orphan nuclear receptors" are also part of the nuclear receptor superfamily, and are structurally homologous to classic nuclear receptors, such as steroid and thyroid receptors. Nucleic acids that encode any of these receptors, or oncogenic forms thereof, can be detected in the methods of the invention. About 40% of all pharmaceutical treatments currently available are agonists or antagonists of nuclear receptors and/or oncogenic forms thereof, underscoring the relative importance of these receptors (and their coding nucleic acids) as targets for analysis by the methods of the invention.

As already mentioned, one preferred class of nucleic acids of interest are those that are diagnostic of colon cancer, e.g., in samples derived from stool. Colon cancer is a common disease that can be sporadic or inherited. The molecular basis of various patterns of colon cancer is known in some detail. In general, germline mutations are the basis of inherited colon cancer syndromes, while an accumulation of somatic mutations is the basis of sporadic colon cancer. In Ashkenazi Jews, a mutation that was previously thought to be a polymorphism may cause familial colon cancer. Mutations of at least three different classes of genes have been described in colon cancer etiology: oncogenes, suppressor genes, and mismatch repair genes. One example nucleic acid encodes DCC (deleted in colon cancer), a cell adhesion molecule with homology to fibronectin. An additional form of colon cancer is an autosomal dominant gene, hMSH2, that comprises a lesion. Familial adenomatous polyposis is another form of colon cancer with a lesion in the MCC locus on chromosome #5. For additional details on Colon Cancer, see, Calvert et al. (2002) "The Genetics of Colorectal Cancer" *Annals of Internal Medicine* 137 (7): 603-612 and the references cited therein. For a variety of colon cancers and colon cancer markers that can be detected in stool, see, e.g., Boland (2002) "Advances in Colorectal Cancer Screening: Molecular Basis for Stool-Based DNA Tests for Colorectal Cancer: A Primer for Clinicians" *Reviews In Gastroenterological Disorders* Volume 2, Supp. 1 and the references cited therein. As with other cancers, mutations in a variety of other genes that correlate with cancer, such as Ras and p53, are useful diagnostic indicators for cancer.

Cervical cancer is another preferred target for detection, e.g., in samples obtained from vaginal secretions. Cervical cancer can be caused by the papova virus and has two oncogenes, E6 and E7. E6 binds to and removes p53 and E7 binds to and removes PRB. The loss of p53 and uncontrolled action of E2F/DP growth factors without the regulation of pRB is one mechanism that leads to cervical cancer.

Another preferred target for detection by the methods of the invention is retinoblastoma, e.g., in samples derived from tears. Retinoblastoma is a tumor of the eyes which results from inactivation of the pRB gene. It has been found to transmit heritably when a parent has a mutated pRB gene (and, of course, somatic mutation can cause non-heritable forms of the cancer).

Neurofibromatosis Type 1 can be detected in the methods of the invention. The NF1 gene is inactivated, which activates the GTPase activity of the ras oncogene. If NF1 is missing, ras is overactive and causes neural tumors. The methods of the invention can be used to detect Neurofibromatosis Type 1 in CSF or via tissue sampling.

Many other forms of cancer are known and can be found by detecting associated genetic lesions using the methods of the invention. Cancers that can be detected by detecting appropriate lesions include cancers of the lymph, blood, stomach, gut, colon, testicles, pancreas, bladder, cervix, uterus, skin, and essentially all others for which a known genetic lesion exists. For a review of the topic, see, *The Molecular Basis of Human Cancer* Coleman and Tsongalis (Eds) Humana Press; ISBN: 0896036340; 1st edition (August 2001).

Similarly, nucleic acids from pathogenic or infectious organisms can be detected by the methods of the invention, e.g., for infectious fungi, e.g., *Aspergillus*, or *Candida* species; bacteria, particularly *E. coli*, which serves a model for pathogenic bacteria (and, of course certain strains of which are pathogenic), as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxoviruses, e.g., RSV; Orthomyxoviruses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

A variety of nucleic acid encoding enzymes (e.g., industrial enzymes) can also be detected according to the methods herein, such as amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases. Similarly, agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase can also be detected.

Aliquotting the Sample

The sample can be aliquotted and/or diluted using standard or microfluidic fluid handling approaches (or combinations thereof). Standard fluid handling approaches for dilution/aliquotting include, e.g., pipetting appropriate volumes of the sample into microtiter trays and adding an appropriate diluent. These operations can be performed manually or using available high throughput fluid handlers that are designed to use microtiter trays. High throughput equipment (e.g., incorporating automated pipettors and robotic microtiter tray handling) is preferred, as the present invention contemplates making and using high numbers of aliquots of a sample of interest.

Many automated systems for fluid handling are commercially available and can be used for aliquotting and/or diluting a sample in the context of the present invention. For example, a variety of automated systems are available from the Zymark Corporation (Zymark Center, Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). In any case, a conventional high throughput systems can be used in place of, or in conjunction with microfluidic systems (for example, conventional systems can be used to aliquot samples into microtiter trays, from which microfluidic systems can draw materials) in practicing the methods of the invention.

In one aspect, emulsions are created, where sample aliquots comprise or consist of droplets within the emulsions. The emulsions can be amplified by standard thermocyclic reactions and amplified nucleic acids detected within droplets of the emulsions using standard equipment (e.g., microscope stations or CCD arrays).

Microfluidic systems provide a preferred fluid handling and amplification technology that can conveniently be applied to the present invention. In typical embodiments, samples are drawn into microfluidic devices that comprise networks of microscale cavities (channels, chambers, etc., having at least one dimension less than about 500 µM in size and often less than about 100 µM) and the samples are mixed, diluted, aliquotted or otherwise manipulated in the network of cavities. For example, the microscale device can comprise one or more capillary, in fluid communication with the network, extending outward from a body structure of the microscale device. Negative pressure (vacuum) is applied to the capillary and fluids are drawn into the network from a container (e.g., a well on a microtiter tray). This process can be multiplexed by using a device that comprises multiple capillary channels, permitting many samples to be drawn into the network and processed simultaneously. Sample interfaces with dried samples can also be performed using this basic system, e.g., by partly or completely expelling fluid from the capillary to hydrate samples prior to drawing them into the microfluidic device (the fluid is typically contacted to the samples as a hanging drop on the tip of the capillary and then drawn back into the capillary). For either approach, see also, U.S. Pat. No. 6,482,364 to Parce, et al. (Nov. 19, 2002) MICROFLUIDIC SYSTEMS INCLUDING PIPETTOR ELEMENTS; U.S. Pat. No. 6,042,709 to Parce, et al. (Mar. 28, 2000) MICROFLUIDIC SAMPLING SYSTEM AND METHODS; U.S. Pat. No. 6,287,520 to Parce, et al. (Sep. 11, 2001) ELECTROPIPETTOR AND COMPENSATION MEANS FOR ELECTROPHORETIC BIAS and U.S. Pat. No. 6,235,471 to Knapp, et al. (May 22, 2001) CLOSED-LOOP BIOCHEMICAL ANALYZERS. Essentially any fluid manipulation (aliquotting, diluting, heating and cooling) can be performed in the network using available methods. Details regarding dilution and aliquotting operations in microscale devices can be found in the patent literature, e.g., U.S. Pat. No. 6,149,870 to Parce, et al. (Nov. 21, 2000) APPARATUS FOR IN SITU CONCENTRATION AND/OR DILUTION OF MATERIALS IN MICROFLUIDIC SYSTEMS; U.S. Pat. No. 5,869,004 to Parce, et al. (Feb. 9, 1999) METHODS AND APPARATUS FOR IN SITU CONCENTRATION AND/OR DILUTION OF MATERIALS IN MICROFLUIDIC SYSTEMS; and U.S. Pat. No. 6,440,722 to Knapp, et al. (Aug. 27, 2002) MICROFLUIDIC DEVICES AND METHODS FOR OPTIMIZING REACTIONS. Samples and components to be mixed/diluted or aliquotted can be brought into the microscale device through pipettor elements or from reaction component reservoirs on the device itself, or, commonly, both. For example, the sample can be brought into the microfluidic device through a pipettor channel and diluted and supplied with common reagents from an on device dilution and/or reagent reservoir(s). Locus specific reagents (e.g., amplification primers) can be on the device in wells, or stored off the device, e.g., in microtiter plates (in which case they can be accessed by the pipettor channel). Any or all of these operations can be performed in a continuous or stopped flow format.

The functions the chip performs typically include reaction assembly (assembly of reaction components), thermocycling, and acting as a "cuvette" for an optical system during an imaging step. In the reaction assembly, the reaction mixture components (particularly magnesium and the enzyme) which get combined at the last second before heating begins are assembled. This is called a "hot start" and provides advantages of specificity. During thermocycling, the system optionally provides both constant fluid movement and constant temperature change. During imaging, a high data rate CCD is useful in providing an adequate dynamic range using the dispersion/diffusion methods of quantification.

Commercial systems that perform all aspects of fluid handling and analysis that can be used in the practice of the present invention are available. Examples include the 250 HTS system and AMS 90 SE from Caliper Technologies (Mountain View, Calif.). These systems performs experiments in serial, continuous flow fashion and employ a "chip-to-world" interface, or sample access system, called a sipper through which materials in microwell plates are sipped into a capillary or capillaries attached to the chip and drawn into the channels of the chip. There they are mixed with components of interest and a processing and result detection steps are performed.

Whether conventional fluid handling or microfluidic approaches (or both) are used, the aliquotting and/or dilution events can be performed to achieve particular results. For example, a sample can be diluted equally in each aliquot, or, alternately, the aliquots can be differentially diluted (e.g., a dilution series can be made). The aliquots themselves are of a volume that is appropriate to the fluid handling approach being used by the system, e.g., on the order of a few microliters for microtiter plates to 100 nL, 10 nL or even 1 nL or less for microfluidic approaches.

The aliquots are selected to have high or low copy numbers of any relevant nucleic acid (e.g., for low copy number aliquots, 50 or fewer, generally 25 or fewer, usually 10 or fewer and often 5 or fewer, 2 or fewer or 1 or fewer copies of the relevant nucleic acid(s)). The number of aliquots generated will depend on the size of the sample and the amount of quantitative information desired by the practitioner. For example, where simple detection of a rare nucleic acid is desired, enough low copy number aliquots are made of the sample to detect the nucleic acid in one of the aliquots. Where more quantitative information is needed, enough copies are made to provide reliable statistical information, e.g., to a given confidence value. In either case, this can include anywhere from 1 aliquot to $10^9$ or more aliquots, e.g., 10, 100, 1,000, 10,000, 100,000, 1,000,000, 1,000,000,000 or more aliquots. There is no theoretical limit on the number of aliquots that can be made and assessed for a nucleic acid of interest according to the present invention, though there are practical considerations with respect to the throughput of the system and the size of the sample (the lower the throughput, the fewer aliquots can be analyzed in a given time; the larger the sample size the more aliquots can be made of the sample). Using microfluidic approaches, reagent usage (and concomitant reagent costs) can be minimized. By formatting the system to provide for continuous flow of sample and reagents, including, optionally, during amplification, the systems of the invention can greatly speed the process of searching many different samples for a nucleic acid of interest. Similarly, if stopped flow approaches are used, simultaneous processing of signals from PCR reactions can be used to speed the process of searching samples for a nucleic acid of interest. In the examples below, about 150 aliquots for each dilution range was sufficient to provide reasonable quantitative information for Poisson statistics for model samples. Obviously, more or fewer aliquots can be used in the methods as well.

In many of the embodiments herein, it is worth noting that many of the aliquots will have zero copies of the nucleic acid of interest, due to the rarity of the relevant nucleic acid in the sample (and the dilution that is chosen). This does not present a detection problem in a continuous flow analysis system—the flow rate can be used to calculate how many aliquots have passed (undetected) by a detector prior to detection of the nucleic acid of interest. In non-continuous flow systems (e.g., microwell plate based systems), one can simply count blank reactions (wells lacking amplification product) to determine the frequency of amplification of the nucleic acid of interest. In any event, anywhere from 1 to $10^6$ or more zero copy reactions can be made and assessed by the system, e.g., about 10, 25, 50, 100, 500, 1,000, 10,000, 100,000, or 1,000,000 or more zero copy reactions can be detected in the process of detecting a nucleic acid of interest. Similarly, additional nucleic acids other than the nucleic acid of interest (e.g., controls, or alternate alleles of a nucleic acid of interest that are also amplified by the relevant locus specific reagent) can be detected (or not detected) by the system. The proportion of such alternate nucleic acids in the system to the nucleic acid of interest can range from less than 1 to $10^9$ or more, e.g., 1×, 10×, 100×, 1,000×, 10,000×, 100,000×, 1,000,000×, 1,000,000,000× or more.

Furthermore, as demonstrated in the examples and figures herein, the continuous flow format is a surprisingly efficient system, meaning that a high proportion of single molecules that get into the system get amplified. This efficiency is useful in ensuring that very rare molecules are detected, if present, for example in a biowarfare or infectious disease detection applications. Evidence for high efficiency is in the examples, tables and figures herein. Typically, the systems of the invention can be used to amplify at least 90%, generally 95%, often 99% or more of the rare molecules that are present in sample of interest, or that are present in a collection of aliquots that are subjected to amplification.

Amplifying the Aliquots

The methods of the invention include amplifying a nucleic acid of interest and, optionally, one or more additional nucleic acids. Any available amplification method can be used, including PCR, RT-PCR, LCR, and/or any of the various RNA mediated amplification methods. PCR, RT-PCR and LCR are preferred amplification methods for amplifying a nucleic acid of interest in the methods of the invention. Real time PCR and/or RT-PCR (e.g., mediated via TaqMan™ probes or molecular beacon-based probes) can also be used to facilitate detection of amplified nucleic acids.

It is expected that one of skill is generally familiar with the details of these amplification methods. Details regarding these amplification methods can be found, e.g., in Sambrook (2000); Ausubel (2002) and Innis (1990), all above. Additional details can be found in *PCR: A Practical Approach* (*The Practical Approach Series*) by Quirke et al. (eds.). (1992) by Oxford University Press.

Additional details can also be found in the literature for a variety of applications of PCR. For example, details regarding amplification of nucleic acids in plants can be found, e.g., in *Plant Molecular Biology* (1993) Croy (ed.) BIOS Scientific Publishers, Inc. Similarly, additional details regarding PCR for cancer detection can be found in any of a variety of sources, e.g., Bernard and Wittwer (2002) "Real Time PCR Technology for Cancer Diagnostics *Clinical Chemistry* 48(8):1178-1185; Perou et al. (2000) "Molecular portraits of human breast tumors" *Nature* 406:747-52; van't Veer et al. (2002) "Gene expression profiling predicts clinical outcome of breast cancer" *Nature* 415:530-6; Rosenwald et al. (2001) "Relation of gene expression phenotype to immunoglobulin mutation genotype in B cell chronic lymphocytic leukemia" *J Exp Med* 194:1639-47; Alizadeh et al. (2000) "Distinct types of diffuse large B-cell lymphoma identified by gene expression profiling" *Nature* 403:503-11; Garber et al. (2001) "Diversity of gene expression in adenocarcinoma of the lung" *Proc Natl Acad Sci USA* 98: 13784-9; Tirkkonen et al. (1998) "Molecular cytogenetics of primary breast cancer by CGH" *Genes Chromosomes Cancer* 21:177-84; Watanabe et al. (2001) "A novel amplification at 17q21-23 in ovarian cancer cell lines detected by comparative genomic hybridization" *Gynecol Oncol* 81:172-7, and many others.

Molecular Beacons

In one aspect, real time PCR is performed on the various aliquots or reaction mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched.

Details regarding standard methods of making and using MBs are well established in the literature and MBs are available from a number of commercial reagent sources. See also, e.g., Leone et al. (1995) "Molecular beacon probes combined with amplification by NASBA enable homogenous real-time detection of RNA." *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" *Mol Cell Probes* 11:187-194; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et al. (1999) "Designing a novel molecular beacon for surface-immobilized DNA hybridization studies" *J. Am. Chem. Soc.* 121:2921-2922; Marras et al. (1999) "Multiplex detection of single-nucleotide variation using molecular beacons" *Genet. Anal. Biomol. Eng.* 14:151-156; and Vet et al. (1999) "Multiplex detection of four pathogenic retroviruses using molecular beacons" *Proc. Natl. Acad. Sci. U.S.A.* 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

MBs are robust reagents for detecting and quantifying nucleic acids, including in real time, e.g., during PCR, LCR or other nucleic acid amplification reactions (e.g., MBs can be used to detect targets as they are formed). A variety of commercial suppliers produce standard and custom molecular beacons, including Cruachem, Oswel Research Products Ltd. (UK), Research Genetics (a division of Invitrogen, Huntsville Ala., the Midland Certified Reagent Company (Midland, Tex.) and Gorilla Genomics, LLC (Alameda, Calif.). A variety of kits which utilize molecular beacons are also commercially available, such as the Sentinel™ Molecular Beacon Allelic Discrimination Kits from Stratagene (La Jolla, Calif.) and various kits from Eurogentec SA (Belgium) and Isogen Bioscience BV (The Netherlands).

MB components (e.g., oligos, including those labeled with fluorophores or quenchers) can be synthesized using conventional methods. For example, oligos or peptide nucleic acids (PNAs) can be synthesized on commercially available automated oligonucleotide/PNA synthesis machines using standard methods. Labels can be attached to the oligos or PNAs either during automated synthesis or by post-synthetic reactions which have been described before see, e.g., Tyagi and Kramer (1996) "Molecular beacons: probes that fluoresce upon hybridization" Nature Biotechnology 14:303-308 and U.S. Pat. No. 6,037,130 to Tyagi et al (Mar. 14, 2000), entitled "Wavelength-shifting probes and primers and their use in assays and kits." and U.S. Pat. No. 5,925,517 (Jul. 20, 1999) to Tyagi et al. entitled "Detectably labeled dual conformation oligonucleotide probes, assays and kits." Additional details on synthesis of functionalized oligos can be found in Nelson, et al. (1989) "Bifunctional Oligonucleotide Probes Synthesized Using A Novel CPG Support Are Able To Detect Single Base Pair Mutations" Nucleic Acids Research 17:7187-7194. Labels/quenchers can be introduced to the oligonucleotides or PNAs, e.g., by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo)benzoic acid (DABCYL) can be used when the site of attachment is a primary amino group; and 4-dimethylaminophenylazophenyl-4'-maleimide (DABMI) can be used when the site of attachment is a sulphydryl group. Similarly, fluorescein can be introduced in the oligos, either using a fluorescein phosphoramadite that replaces a nucleoside with fluorescein, or by using a fluorescein dT phosphoramadite that introduces a fluorescein moiety at a thymidine ring via a spacer. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonyl-chloride of Texas red coupled to a sulphydryl group. During the synthesis of these labeled components, conjugated oligonucleotides or PNAs can be purified, if desired, e.g., by high pressure liquid chromatography or other methods.

TaqMan™ Probes

PCR quantification using dual-labeled fluorogenic oligo-nucleotide probes, commonly referred to as "TaqMan™" probes, can be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity.

Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes).

General Probe Synthesis Methods

In general, synthetic methods for making oligonucleotides, including probes, molecular beacons, PNAs, LNAs (locked nucleic acids), etc., are well known. For example, oligonucleotides can be synthesized chemically according to the solid phase phosphoramidite triester method described by Beaucage and Caruthers (1981), Tetrahedron Letts., 22(20):1859-1862, e.g., using a commercially available automated synthesizer, e.g., as described in Needham-VanDevanter et al. (1984) Nucleic Acids Res., 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company, The Great American Gene Company, ExpressGen Inc., Operon Technologies Inc. (Alameda, Calif.) and many others. Similarly, PNAs can be custom ordered from any of a variety of sources, such as PeptidoGenic, HTI Bio-products, inc., BMA Biomedicals Ltd (U.K.), Bio Synthesis, Inc., and many others.

Amplification in Microfluidic Systems

A number of high throughput approaches to performing PCR and other amplification reactions have been developed, e.g., involving amplification reactions in microfluidic devices, as well as methods for detecting and analyzing amplified nucleic acids in or on the devices. Details regarding such technology is found, e.g., in the technical and patent literature, e.g., Kopp et al. (1998) "Chemical Amplification: Continuous Flow PCR on a Chip" Science, 280 (5366): 1046; U.S. Pat. No. 6,444,461 to Knapp, et al. (Sep. 3, 2002) MICROFLUIDIC DEVICES AND METHODS FOR SEPARATION; U.S. Pat. No. 6,406,893 to Knapp, et al. (Jun. 18, 2002) MICROFLUIDIC METHODS FOR NON-THERMAL NUCLEIC ACID MANIPULATIONS; U.S. Pat. No. 6,391,622 to Knapp, et al. (May 21, 2002) CLOSED-LOOP BIOCHEMICAL ANALYZERS; U.S. Pat. No. 6,303,343 to Kopf-Sill (Oct. 16, 2001) INEFFICIENT FAST PCR; U.S. Pat. No. 6,171,850 to Nagle, et al. (Jan. 9, 2001) INTEGRATED DEVICES AND SYSTEMS FOR PERFORMING TEMPERATURE CONTROLLED REACTIONS AND ANALYSES; U.S. Pat. No. 5,939,291 to Loewy, et al. (Aug. 17, 1999) MICROFLUIDIC METHOD FOR NUCLEIC ACID AMPLIFICATION; U.S. Pat. No. 5,955,029 to Wilding, et al. (Sep. 21, 1999) MESOSCALE POLYNUCLEOTIDE AMPLIFICATION DEVICE AND METHOD; U.S. Pat. No. 5,965,410 to Chow, et al. (Oct. 12, 1999) ELECTRICAL CURRENT FOR CONTROLLING FLUID PARAMETERS IN MICROCHANNELS; Service (1998) "Microchips Arrays Put DNA on the Spot" *Science* 282:396-399), Zhang et al. (1999) "Automated and Integrated System for High-Throughput DNA Genotyping Directly from Blood" *Anal. Chem.* 71:1138-1145 and many others.

For example, U.S. Pat. No. 6,391,622 to Knapp, et al. (May 21, 2002) CLOSED-LOOP BIOCHEMICAL ANALYZERS and the references cited therein describes systems comprising microfluidic elements that can access reagent storage systems and that can perform PCR or other amplification reactions by any of a variety of methods in the microfluidic system. For example, the microfluidic system can have one or more capillaries extending outwards from the body structure of the microfluidic system for drawing materials into the body structure. Within the body structure are microfluidic cavities (channels, chambers, or the like having at least one dimension smaller than about 500 microns, and, typically smaller than about 100 microns) in which the amplification reactions are performed. The capillaries that extend out from the body structure can access standard reagent storage elements (microtiter plates, or the like) by drawing fluid into the capillary, e.g., due to application of a vacuum or electroosmotic force. Similarly, the capillaries can access dried reagent libraries on substrates (e.g., the LibraryCard™ reagent array made by Caliper Technologies) by partly or completely expelling fluid to rehydrate library members and then by drawing the rehydration fluid back into the capillary. For example, the capillary can partly expel fluid to form a hanging drop on the capillary, which is then contacted to the material to be hydrated. The material in the hanging drop is then drawn back into the capillary. In any case, molecular beacons or TaqMan™ probes can be incorporated into the relevant amplification reaction and detected in the microfluidic device to provide for real time PCR detection. Alternately, PCR amplicons can be detected by conventional methods, such as hybridization to a labeled probe, e.g., prior to or following a separation operation that separates unhybridized probe from hybridized probe. For example, an electrophoretic separation can be performed in a channel of the microscale device.

Conventional High Throughput Systems

In an alternative embodiment, standard fluid handling approaches are used in place of, or in conjunction with, microfluidic approaches. PCR can be performed in standard reaction vessels (e.g., microtiter plates), as can dilutions or other operations relevant to the present invention. Various high-throughput systems are available for non-microfluidic approaches to fluid handling (typically involving plates comprising several reaction chambers, e.g., 96 well, 384 well or 1536 well microtiter plates). These approaches can utilize conventional robotics to perform fluid handling operations and can use conventional commercially available thermocyclers to perform amplification reactions. See above, for a discussion of automated fluid handling systems.

Detecting the Amplified Nucleic Acids

Any available method for detecting amplified nucleic acids can be used in the present invention. Common approaches include real time amplification detection with molecular beacons or TaqMan™ probes, detection of intercalating dyes (ethidium bromide or sybergreen), detection of labels incorporated into the amplification probes or the amplified nucleic acids themselves, e.g., following electrophoretic separation of the amplification products from unincorporated label), and/or detection of secondary reagents that bind to the nucleic acids. Details on these general approaches is found in the references cited herein, e.g., Sambrook (2000), Ausubel (2002), and the references in the sections herein related to real time PCR detection. Additional labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.) (Available on CD ROM).

Amplified nucleic acids (amplicons) can be detected in solution (e.g., using molecular beacons or TaqMan™ probes) or during or after separation (e.g., by electrophoresis). Details on these strategies can be found in the preceding references.

Amplification and detection are commonly integrated in a system comprising a microfluidic device in the present invention. Available microfluidic systems that include detection features for detecting nucleic acids include the 250 HTS system and AMS 90 SE from Caliper Technologies (Mountain View, Calif.), as well as the Agilent 2100 bioanalyzer (Agilent, Palo Alto, Calif.). Additional details regarding systems that comprise detection (and separation/detection) capabilities are well described in the patent literature, e.g., the references already noted herein and in Parce et al. "High Throughput Screening Assay Systems in Microscale Fluidic Devices" WO 98/00231.

In general, the devices herein optionally include signal detectors, e.g., which detect fluorescence, phosphorescence, radioactivity, pH, charge, absorbance, luminescence, temperature, magnetism or the like. Fluorescent detection is especially preferred and generally used for detection of amplified nucleic acids (however, upstream and/or downstream operations can be performed on amplicons, which can involve other detection methods).

The detector(s) optionally monitors one or a plurality of signals from an amplification reaction. For example, the detector can monitor optical signals which correspond to "real time" amplification assay results.

Example detectors include photo multiplier tubes, spectrophotometers, CCD arrays, scanning detectors, microscopes, galvo-scanns and/or the like. Amplicons or other components which emit a detectable signal can be flowed past the detector, or, alternatively, the detector can move relative to the site of the amplification reaction (or, the detector can simultaneously monitor a number of spatial positions corresponding to channel regions, or microtiter wells e.g., as in a CCD array).

The detector can include or be operably linked to a computer, e.g., which has software for converting detector signal information into assay result information (e.g., presence of a nucleic acid of interest), or the like.

Signals are optionally calibrated, e.g., by calibrating the microfluidic system by monitoring a signal from a known source.

A microfluidic system can also employ multiple different detection systems for monitoring a signal in the system. Detection systems of the present invention are used to detect and monitor the materials in a particular channel region (or other reaction detection region). Once detected, the flow rate and velocity of cells in the channels are also optionally measured and controlled as described above.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally spectrophotometers, photodiodes, avalanche photodiodes, photomultiplier tubes, diode arrays, or in some cases, imaging systems, such as charged coupled devices (CCDs) and the like. The detection system is typically coupled to a computer, via an analog to digital or digital to analog converter, for transmitting detected light data to the computer for analysis, storage and data manipulation.

In the case of fluorescent materials such as labeled amplicons, the detector typically includes a light source that produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources are used in other detection systems. For example, broad band light sources are typically used in light scattering/transmissivity detection schemes, and the like. Typically, light selection parameters are well known to those of skill in the art.

The detector can exist as a separate unit, but can also be integrated with the system or microfluidic device, into a single instrument. Integration of these functions into a single unit facilitates connection of these instruments with the computer, by permitting the use of few or a single communication port(s) for transmitting information between the controller, the detector and the computer.

Counting and Statistically Analyzing the Nucleic Acid of Interest

One feature of the present invention is that it provides for robust quantitation of rare (and other) nucleic acids in a sample. This robust quantitation provides the ability to perform statistical or probabilistic analysis of the sample. For example, Poisson analysis, Monte Carlo analysis, application of genetic algorithms, neural network training, Markov modeling, hidden Markov modeling, multidimensional scaling, partial least squares (PLS) analysis, or principle component analysis (PCA) can all be applied to data generated by the present invention. These statistical evaluations can be used to determine the concentration or abundance of a given nucleic acid in a sample and to correlate abundance to diagnosis or prognosis associated with the diagnosis or prognosis.

General references that are useful in understanding how to generate and analyze data, as well as other relevant concepts include: Neil Weiss (1999) *Introductory Statistics & Elementary Statistics* Edition: $5^{th}$ ISBN:0201434490; Berinstein (1998) *Finding Statistics Online: How to Locate the Elusive Numbers You Need*. Medford, N.J.: Information Today; Everitt, (1998) *The Cambridge Dictionary of Statistics* New York: Cambridge University Press; Kotz (1988). *Encyclopedia of Statistical Sciences*, vol. 1-9 plus supplements New York: Wiley; Dillon and Goldstein (1984). *Multivariate Analysis: Methods and Applications* New York: Wiley; Tabachnick and Fidell (1996) *Using Multivariate Statistics* New York: HarperCollins College Publishers; Box et al. (1978) *Statistics for Experimenters* New York: Wiley; Cornell (1990) *Experiments with Mixtures* New York: Wiley; John, P. W. M. (1998) *Statistical Design and Analysis of Experiments* Philadelphia: SIAM; Gibas and Jambeck (2001) *Bioinformatics Computer Skills* O'Reilly, Sebastipol, Calif.; Pevzner (2000) *Computational Molecular Biology and Algorithmic Approach*, The MIT Press, Cambridge Mass.; Durbin et al. (1998) *Biological Sequence Analysis: Probabilistic Models of Proteins and Nucleic Acids*, Cambridge University Press, Cambridge, UK; and Rashidi and Buehler (2000) *Bioinformatic Basics: Applications in Biological Science and Medicine* CRC Press LLC, Boca Raton, Fla.

Calculating Diffusion and Dispersion

One feature of the invention is the discovery that the highly reproducible peak shape, e.g., amplitude and/or width and/or other shape features of a signal from an amplification reaction can be correlated to the starting copy number for the reaction and/or used to discriminate signals of interest from background fluctuations. This correlation can be performed at the theoretical level, taking thermal diffusivity and Taylor Aris diffusion into account, or it can be performed by comparison to standards (e.g., comparisons to peak shapes, e.g., heights, widths, or general shape profiles for amplification reactions that have known copy numbers for starting materials).

For theoretical calculation approaches, a label is typically initially confined in a region $-h<x<h$, as a function of time (t) and spatial position (x) with respect to the peak center (x=0) and the concentration (C) of the label, or of a component corresponding to the label (e.g., the nucleic acid of interest), is equal to $\frac{1}{2} C_o \{erf[(h-x)/(2Dt)^{1/2})]\}$, where $C_o$ is the initial concentration at time t=0, erf is an error function, and D is a coefficient of overall dispersion. D is equal to the sum of thermal diffusion and Taylor dispersion ($D_T$) in the system. In turn, the Taylor dispersion ($D_T$) is dependent on the dimensions and shape of the microfluidic cavity through which the label is flowed, the flow velocity (u) and the thermal diffusivity (D). Typically, $D=K(d^2u^2)/D$, where K is a proportionality factor which is a function of the microfluidic cavity through which the label is flowed and d is a characteristic microfluidic cavity length. For example, where the microfluidic cavity is a circular channel and K=1/192, d is the diameter of the circular channel and $D=D+D_T$. Further details on thermal diffusivity and Taylor Aris dispersion can be found in MICROFLUIDIC SYSTEMS AND METHODS FOR DETERMINING MODULATOR KINETICS, U.S. Ser. No. 09/609,030 By Andrea Chow, Filed Jun. 30, 2000.

Additional System Details

The systems of the invention can include microfluidic devices, detectors, sample storage elements (microtiter plates, dried arrays of components, etc.), flow controllers, amplification devices or microfluidic modules, computers and/or the like. These systems can be used for aliquoting, amplifying and analyzing the nucleic acids of interest. The microfluidic devices, amplification components, detectors and storage elements of the systems have already been described in some detail above. The following discussion describes appropriate controllers and computers, though many configurations are available and one of skill would be expected to be familiar in their use and would understand how they can be applied to the present invention.

Flow Controllers

A variety of controlling instrumentation is optionally utilized in conjunction with the microfluidic devices described herein, for controlling the transport and direction of fluids and/or materials within the devices of the present invention, e.g., by pressure-based or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, Lamb wave pumps and the like that have been described in the art. See, e.g., U.S. Pat. Nos. 5,271,724, 5,277,556, and 5,375,979 and Published PCT Application Nos. WO 94/05414 and WO 97/02357. The systems described herein can also utilize electrokinetic material direction and transport systems.

Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which a microfluidic device is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also optionally used to provide for electrokinetic injection or withdrawal of material downstream of the region of interest to control an upstream flow rate. The same instrumentation and techniques described above are also utilized to inject a fluid into a downstream port to function as a flow control element.

Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates (including for continuous flow), temperatures, applied voltages, and the like.

The systems and/or kits can include system instructions (e.g., embodied in a computer or in a computer readable medium, e.g., as system software) for practicing any of the method steps herein. For example, the system optionally includes system software that correlates a shape, length, width, volume and/or area occupied by amplified copies of the nucleic acid of interest, as detected by the detector, to the number of copies of the nucleic acid of interest present in one of the aliquots, or to the number of copies of the nucleic acid of interest present in the sample, or both. Similarly, the system optionally includes system instructions that direct the dilution module to aliquot the sample into a plurality of aliquots, including a plurality of zero copy aliquots comprising no copies of the nucleic acids of interest and one or more single copy aliquot comprising a single copy of the nucleic acid of interest.

The statistical functions noted above can also be incorporated into system software, e.g., embodied in the computer, in computer memory or on computer readable media. For example, the computer can include statistical or probabilistic system software that performs one or more statistical or probabilistic analysis of signals received from one or more of the aliquots subjected to amplification (e.g., via thermocycling). For example, the statistical or probabilistic analysis can include Poisson analysis, Monte Carlo analysis, application of a genetic algorithm, neural network training, Markov modeling, hidden Markov modeling, multidimensional scaling, PLS analysis, and/or PCA analysis. The statistical or probabilistic analysis software optionally quantitatively determines a concentration, proportion, or number of the nucleic acids of interest in the sample.

In the present invention, the computer typically includes software for the monitoring of materials in the channels. Additionally, the software is optionally used to control electrokinetic or pressure modulated injection or withdrawal of material. The injection or withdrawal is used to modulate the flow rate as described above, to mix components, and the like.

Example System

Figure 6:
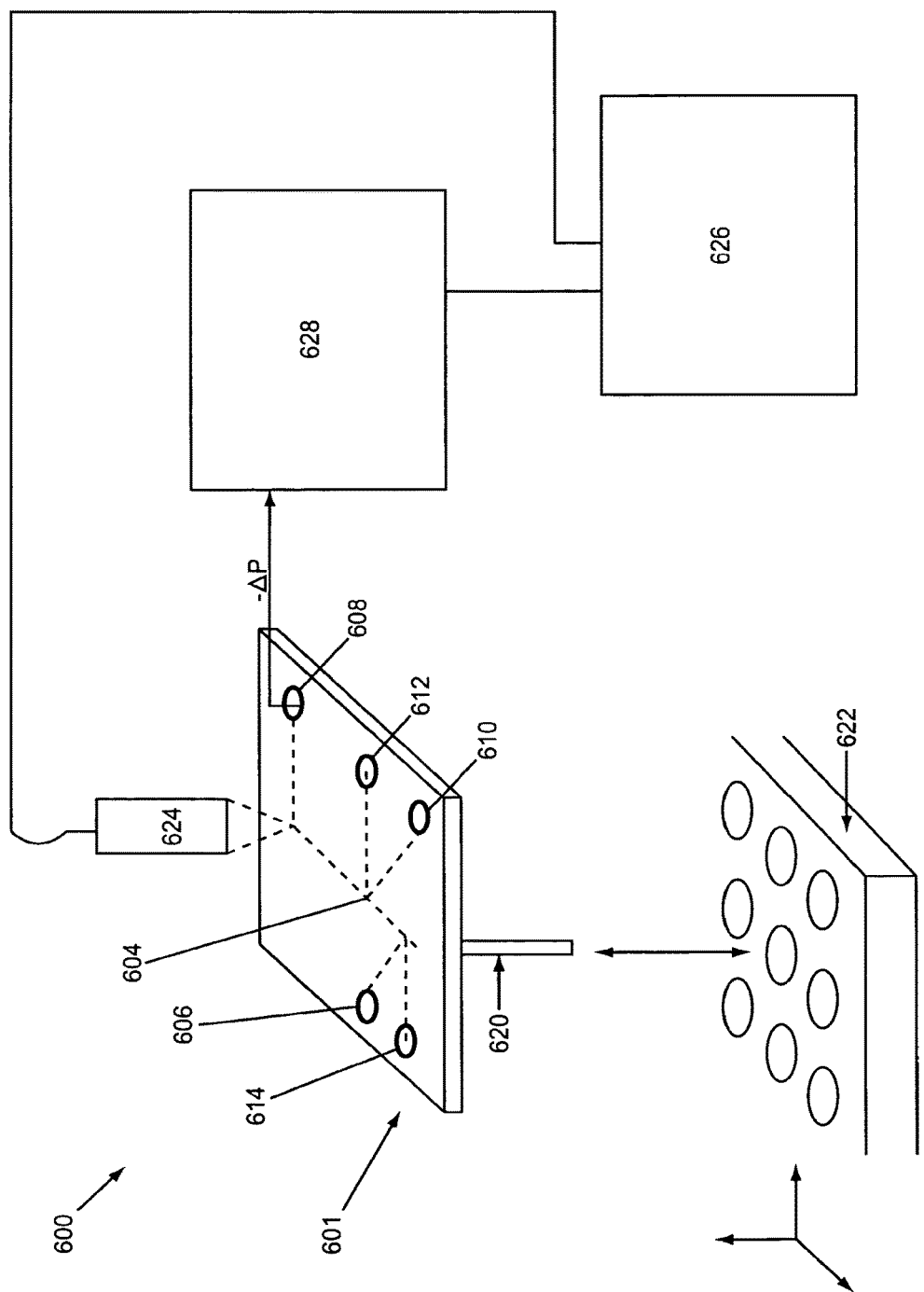
FIG. 6 is a schematic representation of a system of the invention.
Figure 7:
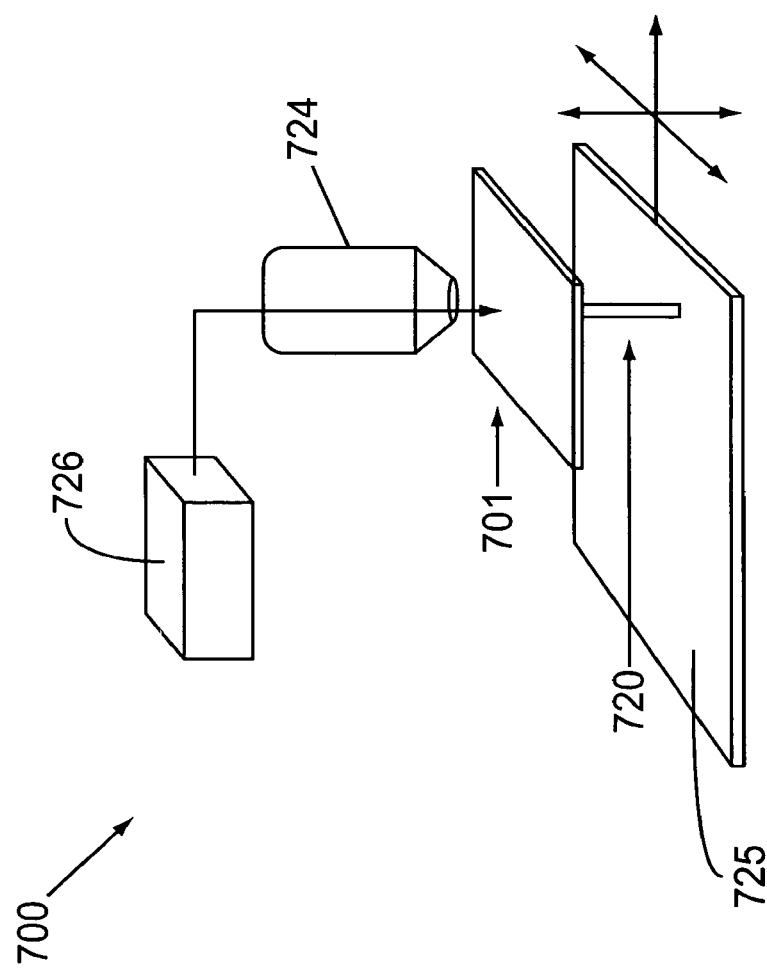
FIG. 7 is a schematic representation of a system of the invention.

FIGS. 6 and 7 provide a schematic illustration of a model system of the invention. As shown in FIG. 6, system 600 includes microfluidic device 601. Device 601 includes main channel 604 fabricated therein. Amplification components are flowed, e.g., from reservoir 606, e.g., by applying a vacuum at vacuum source 608 (and/or at any of the reservoirs or wells noted below) through main channel 604. Amplification components can also be flowed from wells 610 or 612 and into main channel 604. Materials can be also flowed from wells 606 or 608, or materials can be flowed into these wells, e.g., when they are used as waste wells, or when they are coupled to a vacuum source. Flow from wells 614, 612, 610, 606, or 608 can be performed by modulating fluid pressure, or by electrokinetic approaches. Instead of the arrangement of channels depicted in FIGS. 6 and 7, an arrangement such as the device of FIG. 1 can be substituted. A variety of other appropriate microfluidic configurations are set forth in the references noted herein.

Materials relevant to performing the amplification reactions can be flowed from the enumerated wells, or can be flowed from a source external to Device 601. As depicted, the integrated system can include pipettor channel 620, e.g., protruding from device 601, for accessing an outside source of reagents. For example, as depicted, pipettor channel 620 can access microwell plate 622 which includes samples or sample aliquots, or locus specific reagents, or other reagents useful in the practice of the invention in the wells of the plate. Aliquots or reagents relevant to amplification can be flowed into channel 604 through pipettor channel 620. Detector 624 is in sensory communication with channel 604, detecting signals resulting, e.g., from the interaction of a label with an amplicon as described above. Detector 624 is operably linked to Computer 626, which digitizes, stores and manipulates signal information detected by detector 624.

Voltage/pressure controller 628 controls voltage, pressure, or both, e.g., at the wells of the system, or at vacuum couplings fluidly coupled to channel 604 (or the other channels noted above). Optionally, as depicted, computer 626 controls voltage/pressure controller 628. In one set of embodiments, computer 626 uses signal information to select further reaction parameters. For example, upon detecting amplification of a nucleic acid of interest in a well from plate 622, the computer optionally directs withdrawal of additional aliquots from the well for analysis through pipettor channel 620, e.g., to deliver different concentrations of the aliquot to the amplification reaction. Similarly, upon determining that no nucleic acid is present (a zero copy reaction) computer 626 can direct controller 628 to process another aliquot. If statistical information is desired, computer 626 directs controller 628 to perform appropriate fluid manipulations to generate enough data for the statistical analysis. Computer 626 is optionally coupled to or comprises a user viewable display, permitting control of the computer by the user and providing a readout for the user to view results detected by the system.

FIG. 7 depicts an alternate embodiment, in which a solid phase array of reagents or samples is accessed by a microfluidic system. As shown in FIG. 7, system 700 includes microfluidic device 701. Device 701 includes pipettor channel 720 and a microfluidic network fabricated within the device. Amplification components are flowed through device 701, typically by applying pressure (positive or negative) and/or electrokinetic pressure in the microfluidic network.

As depicted, the integrated system can include pipettor channel 720, e.g., protruding from device 701, for accessing an outside source of reagents. For example, as depicted, pipettor channel 720 can access solid phase array 725 which includes samples or sample aliquots, or locus specific reagents, or other reagents useful in the practice of the invention. Fluids are partly or completely expelled from channel 720 to rehydrate materials on array 725. For example, channel 720 can comprise a hanging drop that is used to rehydrate materials, with the drop being withdrawn into channel 720 for distribution into microfluidic device 701. Detector 724 is in sensory communication with device 701 and computer/controller 726. Computer/controller 726 can be operated in a manner similar to computer 626 of FIG. 6. In either case, computer 626 or computer controller 726 optionally control movement of tray 622 or array 725, and/or microfluidic device 601 or 701 to permit the relevant pipettor channel to process samples or other materials on the array or in the wells of the tray.

Many variations of the above system are also appropriate. For example, many types of heating systems can be used in the present invention. For example, winding the channel around fixed heating areas can be performed. Robotics or fluid system elements can be used to heat fluids in multiple different temperature water baths (e.g., 3 baths for a typical amplification reaction at typical annealing, reaction and dissociation conditions).

Additional Kits Details

The present invention also provides kits for carrying out the methods described herein. In particular, these kits typically include system components described herein, as well as additional components to facilitate the performance of the methods by an investigator.

The kit also typically includes a receptacle in which the system component is packaged. The elements of the kits of the present invention are typically packaged together in a single package or set of related packages. The package optionally includes reagents used in the assays herein, e.g., buffers, amplification reagents, standard reagents, and the like, as well as written instructions for carrying out the assay in accordance with the methods described herein. In the case of prepackaged reagents, the kits optionally include pre-measured or pre-dosed reagents that are ready to incorporate into the methods without measurement, e.g., pre-measured fluid aliquots, or pre-weighed or pre-measured solid reagents that may be easily reconstituted by the end-user of the kit.

Generally, the microfluidic devices described herein are optionally packaged to include reagents for performing the device's preferred function. For example, the kits can include any of microfluidic devices described along with assay components, reagents, sample materials, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Single Molecule Amplification and Detection of DNA in a Microfluidic Format

Introduction

The amplification of a desired region of DNA by polymerase chain reaction (PCR) has revolutionized the field of molecular biology. In conventional formats of PCR, which use many microliters of fluids during amplification, the starting DNA copy number is typically at least hundreds to tens of thousands of molecules. Recent advances in microfluidics have demonstrated that it is feasible to miniaturize PCR down by a thousand fold to a nanoliter-reaction volume range. When the sample concentration remains constant, the starting number of DNA template in such a small volume can drop below a cutoff copy number that could be considered statistically unacceptable in some applications. For instance, in single nucleotide polymorphism (SNP) analysis, if the starting copy number is too low (below about a few tens of copies), the amplification of the two different alleles from a heterozygous sample may not amplify equally in quantity due to statistical fluctuations, possibly causing uncertainty in a correct SNP identification for that sample.

In the theoretical limit, only one DNA copy is necessary as a starting template for a PCR reaction. From such a reaction, the amplified products is a pure "clone" of a single parent DNA template, instead of a mixture of many DNA parent templates. Single molecule amplification and detection results in some interesting applications that are not achievable otherwise. One such application is the detection of cancer genes. This example describes (1) a method to perform single molecule PCR using microfluidic technology, (2) analysis and detection of single molecule amplification, and (3) example applications using single molecule PCR detection for cancer detection.

We have experimentally demonstrated that single molecule PCR is possible in a microfluidic channel. In experiments in the absence of flow, there is evidence in support of single molecule PCR in that localized "clouds" of fluorescent probes (corresponding to amplification products) were observed along the heated channel. The evidence for single molecule PCR is more definitive in a sipper chip continuous flow format, in which a very large number of experiments can easily be conducted to obtain adequate statistics to support experimental observations.

Continuous Flow Protocol

Using a sipper chip as shown in the chip design schematic of FIG. 1, a DNA sample (e.g., a genomic DNA) was brought onto chip 100 through a sipper using a pressure gradient into distribution channel 105. Under continuous flow, in an assembly-line fashion, the sample was first mixed with a common reagent from an on-chip reagent reservoir through common reagent channel 106, then split into 8 equal aliquots into 8 independent analysis channels 110-118. Each aliquot was mixed with locus-specific reagents supplied from a channel-specific chip reservoir, then flowed through heated region 130 comprising metal traces proximal to channels 110-118 to provide controlled heated regions of chip 100. Reagent addition for channel specific reagents into channels 110-118 provides an elegant microfluidic method of providing for an on-chip "hot start," in which all of the reagents are added to analysis channels just before amplification. The temperature of the region was cycled appropriately (temperature set points and respective dwell times are controlled) for PCR conditions in the channels in heated region 130. Heated channel lengths and fluid velocity are chosen such that the total PCR cycles meet a desired number, usually between 25 to 40 cycles (though inefficient PCR approaches that have short cycle times and high cycle numbers can also be used; See also, U.S. Pat. No. 6,303,343 to Kopf-Sill (Oct. 16, 2001) entitled INEFFICIENT FAST PCR). 8 channel detection region 135 comprises an appropriate detector for detecting PCR amplicons in channels 110-118.

Amplification and Detection of Rare Molecules

We used the PCR sipper chip illustrated in FIG. 1 to demonstrate single molecule PCR amplification, experimentally, in a continuous flow format. DNA samples with increasing dilution, in concentrations down to less than 1 molecule per nL, were prepared in a microtiter plate which supplies the samples to the sipper (on chip dilution could be performed in alternate embodiments). Due to statistical fluctuations in sampling very low concentration DNA down to below one molecule per channel, it is expected that some channels will show amplification signals and some will not. The fraction of tests at which amplification is observed is best described by Poisson statistics.

Figure 2:
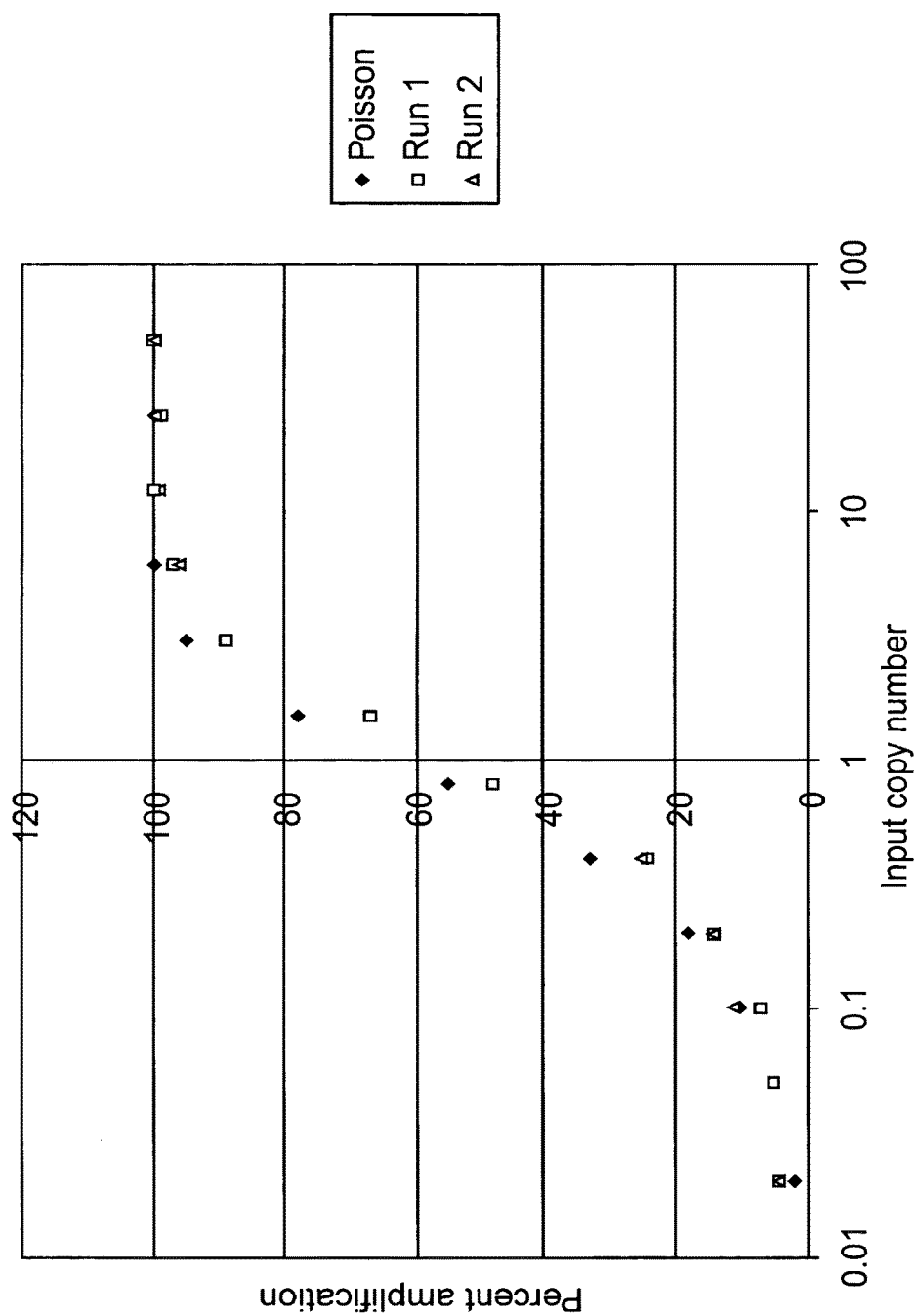
FIG. 2 is a graph of percent amplification versus input copy number for 2 experimental runs, with a comparison to a predicted (Poisson) value.

Table 1 summarizes results of a set of PCR experiments when the average copy number of DNA in each of the 8 channels varied from 0.02 to 48. For each DNA concentration, 8 PCR experiments were done simultaneously. The number of occurrences of a measurable PCR fluorescent signal for each sample was recorded in Table 1, with the maximum occurrence being 8 and the minimum being 0. The percent of occurrence of PCR was calculated and compared with a Poisson statistics prediction. A very good agreement between the measured and predicted percent occurrence of PCR was found. Table 2 summarizes a replication of similar sets of experiments on another day. FIG. 2 is a graphical comparison of predicted (Poisson) and measured statistics (Run 1 and 2) for both sets of experiments. Predicted and actual measurements show close agreement.

TABLE 1

AVERAGE NUMBER OF COPIES IN THE CHANNEL

| PASS | PLATE | | | | | | | | | | | |
|---|---|---|---|---|---|---|---|---|---|---|---|---|
| | 0.02 | 0.05 | 0.1 | 0.2 | 0.4 | 0.8 | 1.5 | 3 | 6 | 12 | 24 | 48 |
| 1 | 0 | 0 | 0 | 2 | 2 | 3 | 5 | 6 | 6 | 8 | 8 | 8 |
| 2 | 0 | 0 | 3 | 0 | 0 | 5 | 7 | 8 | 8 | 8 | 8 | 8 |
| 3 | 0 | 0 | 1 | 1 | 2 | 2 | 5 | 7 | 8 | 8 | 8 | 8 |
| 4 | 2 | 0 | 0 | 1 | 3 | 2 | 5 | 7 | 8 | 8 | 8 | 8 |
| 5 | 0 | 0 | 2 | 0 | 1 | 4 | 3 | 7 | 8 | 8 | 8 | 8 |
| 6 | 1 | 0 | 2 | 2 | 3 | 5 | 5 | 7 | 7 | 8 | 8 | 8 |
| 7 | 2 | 1 | 0 | 0 | 3 | 3 | 5 | 7 | 8 | 8 | 8 | 8 |
| 8 | 0 | 3 | 1 | 4 | 1 | 2 | 6 | 7 | 8 | 8 | 7 | 8 |
| 9 | 1 | 2 | 0 | 3 | 1 | 5 | 8 | 7 | 7 | 8 | 8 | 8 |
| 10 | 0 | 1 | 0 | 1 | 2 | 5 | 7 | 8 | 8 | 8 | 8 | 8 |
| 11 | 0 | 0 | 0 | 1 | 4 | 4 | 5 | 7 | 8 | 8 | 8 | 8 |
| 12 | 0 | 0 | 0 | 0 | 3 | 8 | 7 | 8 | 8 | 8 | 8 | 8 |
| 13 | 0 | 0 | 0 | 1 | 3 | 3 | 5 | 7 | 8 | 8 | 8 | 8 |
| 14 | 0 | 0 | 1 | 1 | 2 | 3 | 6 | 6 | 8 | 8 | 8 | 8 |
| 15 | 0 | 0 | 0 | 0 | 2 | 6 | 6 | 8 | 8 | 8 | 8 | 8 |
| 16 | 0 | 0 | 0 | 0 | 1 | 5 | 3 | 8 | 8 | 8 | 8 | 8 |
| 17 | 0 | 0 | 0 | 0 | 0 | 2 | 5 | 6 | 8 | 8 | 8 | 8 |
| 18 | 0 | 1 | 0 | 2 | 2 | 4 | 4 | 7 | 8 | 8 | 8 | 8 |
| 19 | 0 | 0 | 0 | 2 | 1 | 2 | 5 | 8 | 8 | 8 | 8 | 8 |
| TOTAL | 6 | 8 | 10 | 21 | 36 | 73 | 102 | 136 | 148 | 152 | 151 | 152 |
| POSSIBLE | 152 | 152 | 152 | 152 | 152 | 152 | 152 | 152 | 152 | 152 | 152 | 152 |
| (actual/possible) % | 4% | 5% | 7% | 14% | 24% | 48% | 67% | 89% | 97% | 100% | 99% | 100% |
| POISSON PREDICT | 2% | 5% | 10% | 18% | 33% | 55% | 78% | 95% | 100% | 100% | 100% | 100% |

TABLE 2

AVERAGE NUMBER OF COPIES IN THE CHANNEL

| PASS | PLATE | | | | | | | | | | | |
|---|---|---|---|---|---|---|---|---|---|---|---|---|
| | 0.02 | 0.05 | 0.1 | 0.2 | 0.4 | 0.8 | 1.5 | 3 | 6 | 12 | 24 | 48 |
| 1 | 0 | 0 | 1 | 1 | 5 | 4 | 5 | 7 | 8 | 8 | 8 | 8 |
| 2 | 1 | 1 | 0 | 2 | 2 | 3 | 5 | 6 | 7 | 8 | 8 | 8 |
| 3 | 0 | 0 | 2 | 2 | 2 | 3 | 2 | 8 | 8 | 8 | 8 | 8 |
| 4 | 1 | 0 | 0 | 0 | 3 | 3 | 5 | 5 | 8 | 8 | 8 | 8 |
| 5 | 0 | 0 | 1 | 1 | 1 | 2 | 5 | 8 | 8 | 8 | 8 | 8 |
| 6 | 0 | 0 | 0 | 2 | 2 | 3 | 4 | 8 | 7 | 8 | 8 | 8 |
| 7 | 0 | 0 | 0 | 2 | 1 | 4 | 5 | 7 | 8 | 8 | 8 | 8 |
| 8 | 0 | 1 | 2 | 0 | 0 | 3 | 5 | 6 | 8 | 8 | 8 | 8 |
| 9 | 0 | 0 | 0 | 2 | 1 | 2 | 3 | 6 | 8 | 8 | 8 | 8 |
| 10 | 1 | 0 | 0 | 0 | 3 | 1 | 4 | 6 | 7 | 8 | 8 | 8 |
| 11 | 0 | 0 | 1 | 0 | 4 | 5 | 5 | 6 | 8 | 8 | 8 | 8 |
| 12 | 0 | 0 | 0 | 2 | 3 | 2 | 3 | 7 | 7 | 7 | 8 | 8 |
| 13 | 3 | 1 | 4 | 0 | 1 | 1 | 4 | 6 | 7 | 8 | 8 | 8 |
| 14 | 0 | 1 | 2 | 1 | 1 | 4 | 7 | 6 | 7 | 8 | 8 | 8 |
| 15 | 0 | 0 | 2 | 1 | 0 | 5 | 4 | 8 | 8 | 8 | 8 | 8 |
| 16 | 0 | 0 | 0 | 1 | 1 | 4 | 3 | 7 | 8 | 8 | 8 | 8 |
| 17 | 0 | 0 | 0 | 2 | 3 | 4 | 4 | 4 | 8 | 8 | 8 | 8 |
| 18 | 0 | 0 | 1 | 0 | 4 | 0 | 6 | 7 | 8 | 8 | 8 | 8 |
| 19 | 0 | 1 | 0 | 1 | 1 | 3 | 2 | 8 | 8 | 8 | 8 | 8 |
| 20 | 1 | 0 | 1 | 3 | 2 | 2 | 4 | 7 | 8 | 8 | 8 | 8 |
| TOTAL | 7 | 5 | 17 | 23 | 40 | 58 | 85 | 133 | 154 | 159 | 160 | 160 |
| POSSIBLE | 160 | 160 | 160 | 160 | 160 | 160 | 160 | 160 | 160 | 160 | 160 | 160 |
| (actual/possible) % | 4% | 3% | 11% | 14% | 25% | 36% | 53% | 83% | 96% | 99% | 100% | 100% |
| POISSON PREDICT | 2% | 5% | 10% | 18% | 33% | 55% | 78% | 95% | 100% | 100% | 100% | 100% |

Figure 3A:
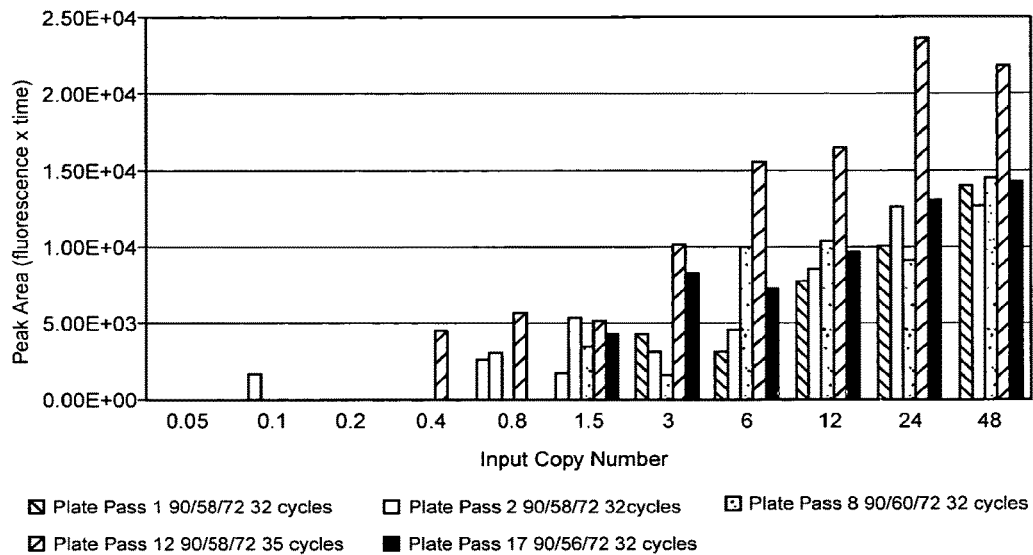
FIG. 3, Panels A and B provide peak area and peak width bar graphs.
Figure 3B:
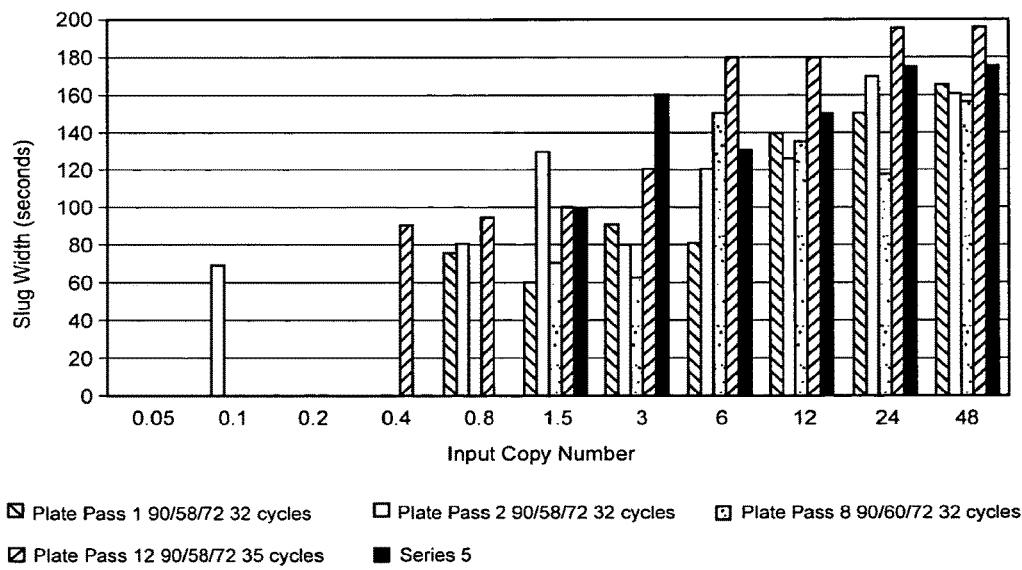
Figure 4A:
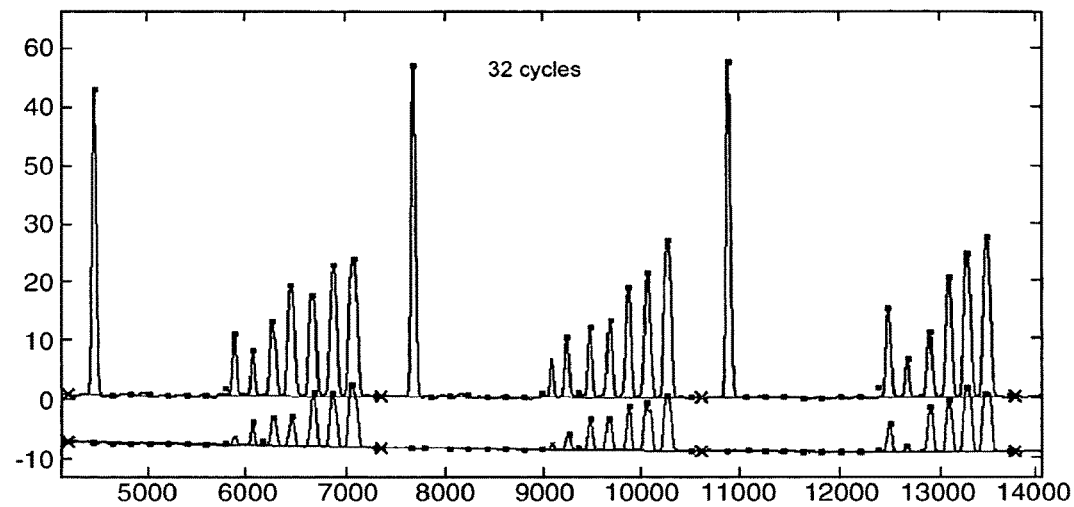
FIG. 4, Panels A-D are graphs illustrating peak width for amplification reactions.
Figure 4B:
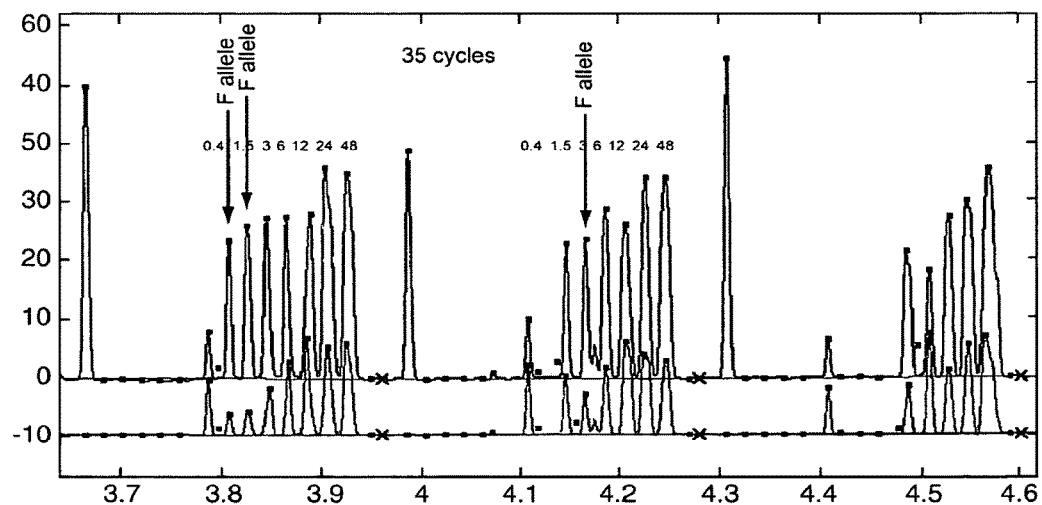
Figure 4C:
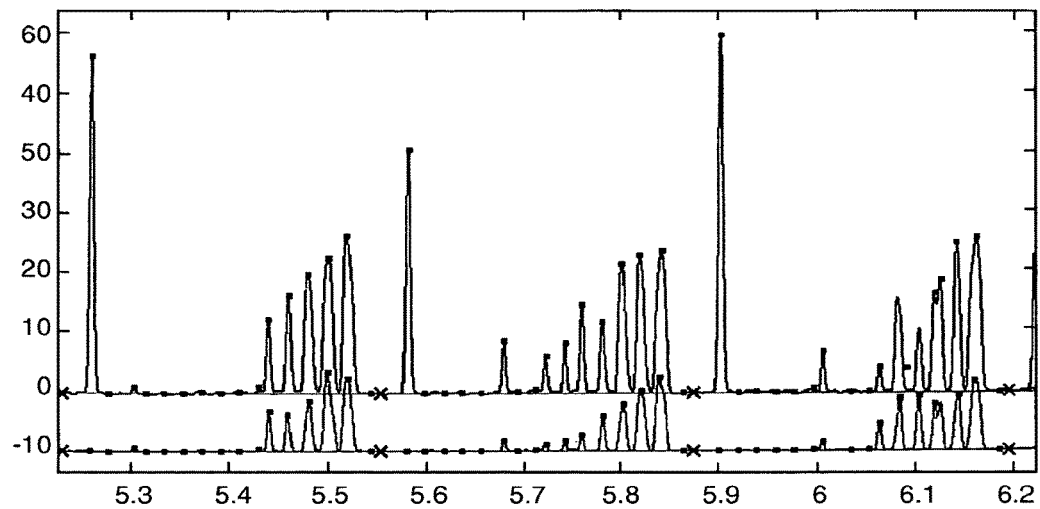
Figure 4D:
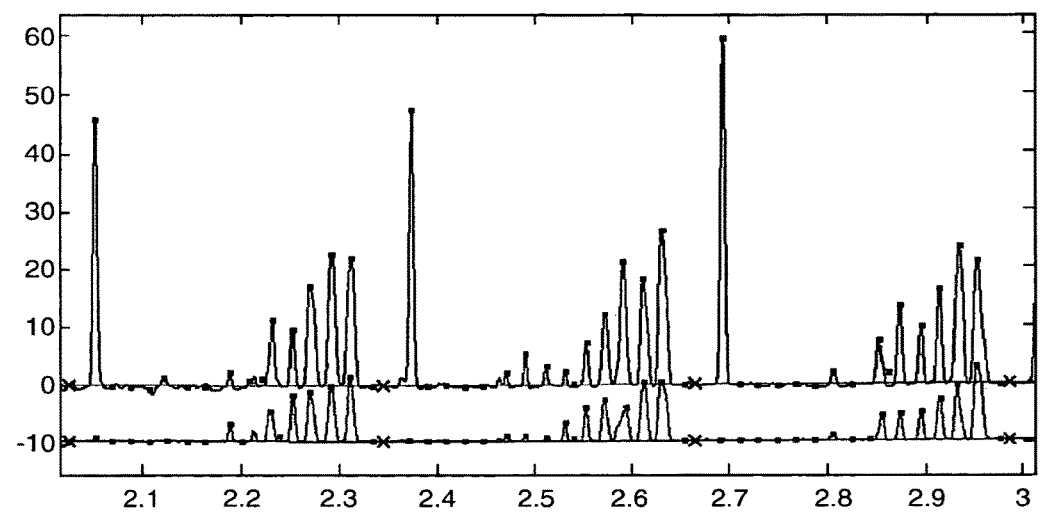

In a continuous flow mode, sipped samples broaden in plug length due to molecular diffusion and flow-induced dispersion. For a sipped sample containing tens or hundreds of copies of starting DNA templates, the effect of diffusion and dispersion on the width of the fluorescence PCR probe region can be predicted by considering Taylor-Aris dispersion. For single molecule PCR, similar calculations can be performed, and the peak shape of the fluorescent product is less broad than a large sample plug counterpart. The narrower peak is mainly due to the starting region from which DNA is amplified being narrower in the single molecule case (a few nm instead of hundreds of μm). FIG. 3 summarizes an analysis of peak area and peak width as a function of starting copy number of DNA in channels. The lower copy number amplifications in fact showed narrow peaks as expected (and vice-versa).

Evidence for the system amplifying and typing single molecules also includes the fact that when the sample is a heterozygote, all peaks are positive for one or the other TaqMan probe, but not both.

There is another use for single molecule typing that can be performed according to the present invention as well. For example, two TaqMan™ or molecular beacon assays can be developed for sequences that are located close together in the genome. Those assays can be used to determine whether the proximal sequences are present on the same amplified molecule. This is an indirect way of doing a sizing assay: one can ask whether individual molecules have both TaqMan™/beacon sites, providing an indication of how often molecules are of a size that encompasses both sites. One can also type the two sites, providing a haplotyping method.

Experiment to Monitor Per Amplification on-Chip by Measuring Fluorescence Generated by Taqman Probe Cleavage.

Figure 5:
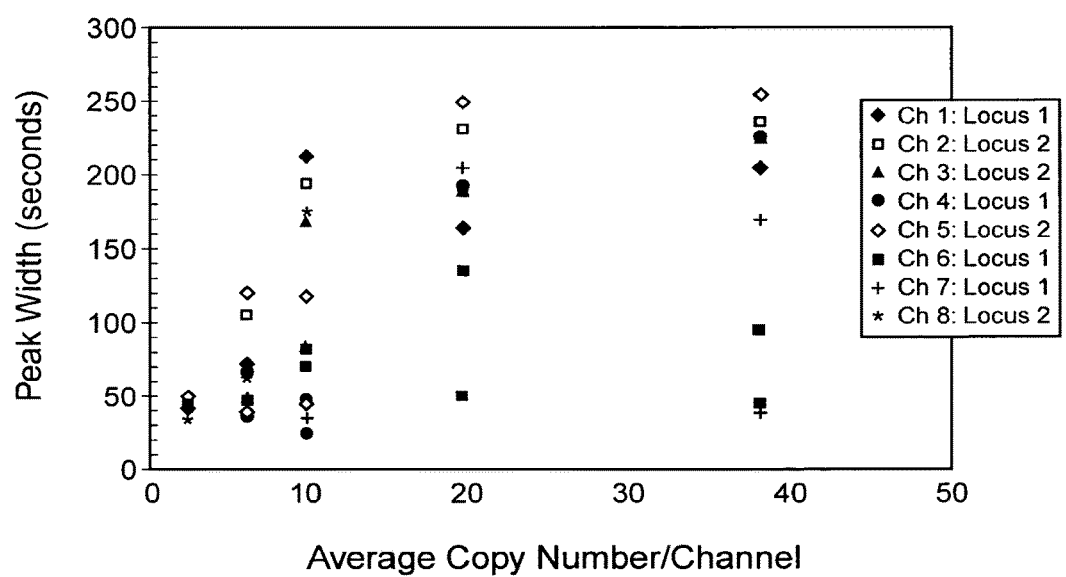
FIG. 5 is a graphical analysis of single molecule amplification peak widths.

This example provides an experiment to monitor PCR amplification on-chip by measuring fluorescence generated by TaqMan probe cleavage. FIG. 5 shows the peak width at ½ max vs. calculated input copy number per channel (on-chip).

For this experiment, all necessary PCR reagents were loaded on-chip. One DNA sample was diluted in assay buffer in a 384-well plate (0.72 ng/µL to 11.5 ng/µL). The amplification cycle time was 17 seconds (5 seconds at 90° C., 7 seconds at 58° C. and 5 seconds at 72° C.) All injected samples were subjected to a total of 35 amplification cycles. Samples were injected for a total of 200 seconds, with a buffer wash (between samples) of 350 seconds. Width of PCR signal (peak) was measured at ½ the peak maximum for each microfluidic channel on-chip (8 total). Data shows that amplification of a single molecule in any channel produces the same width, in time (approximately 40-50 seconds). As more molecules (copies) are injected onto the chip, they begin to overlap, causing the width of the peak to increase in time. However, with long injection times, some single molecules show up on the edges of the injected slug of DNA.

Application of Methods to Allele Typing

In cancer research, detection of cancer genes is very difficult because the mutated gene usually occurs at a much lower concentration then the wild type in a sample. The ability to detect amplification from a single molecule would solve the problem of detecting a low concentration of a mutated gene with a high concentration of wild type in the background since one can now study a single clone at a time. The use of the microfluidic sipper chip format with parallelized PCR on the chip speeds up the rate at which a single clone is examined at a time, to the point where it is practical to do a massive number of PCRs to find the few mutated genes responsible for cancer that exist in a given sample. FIG. 4 illustrates raw fluorescence intensity measurements for SNP analysis at very low starting copy number to below 1 copy per channel on average. These data show the possibility of detecting SNP at single molecule PCR conditions.

Figure 10:
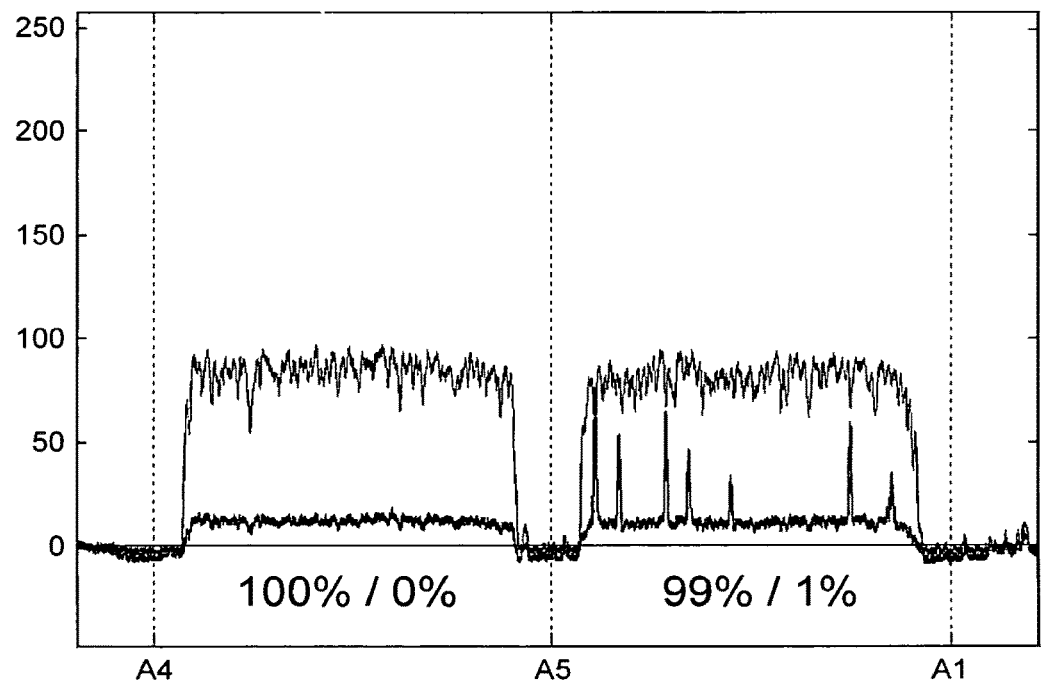
FIG. 10 is a data graph showing single molecule DNA amplification.
Figure 11:
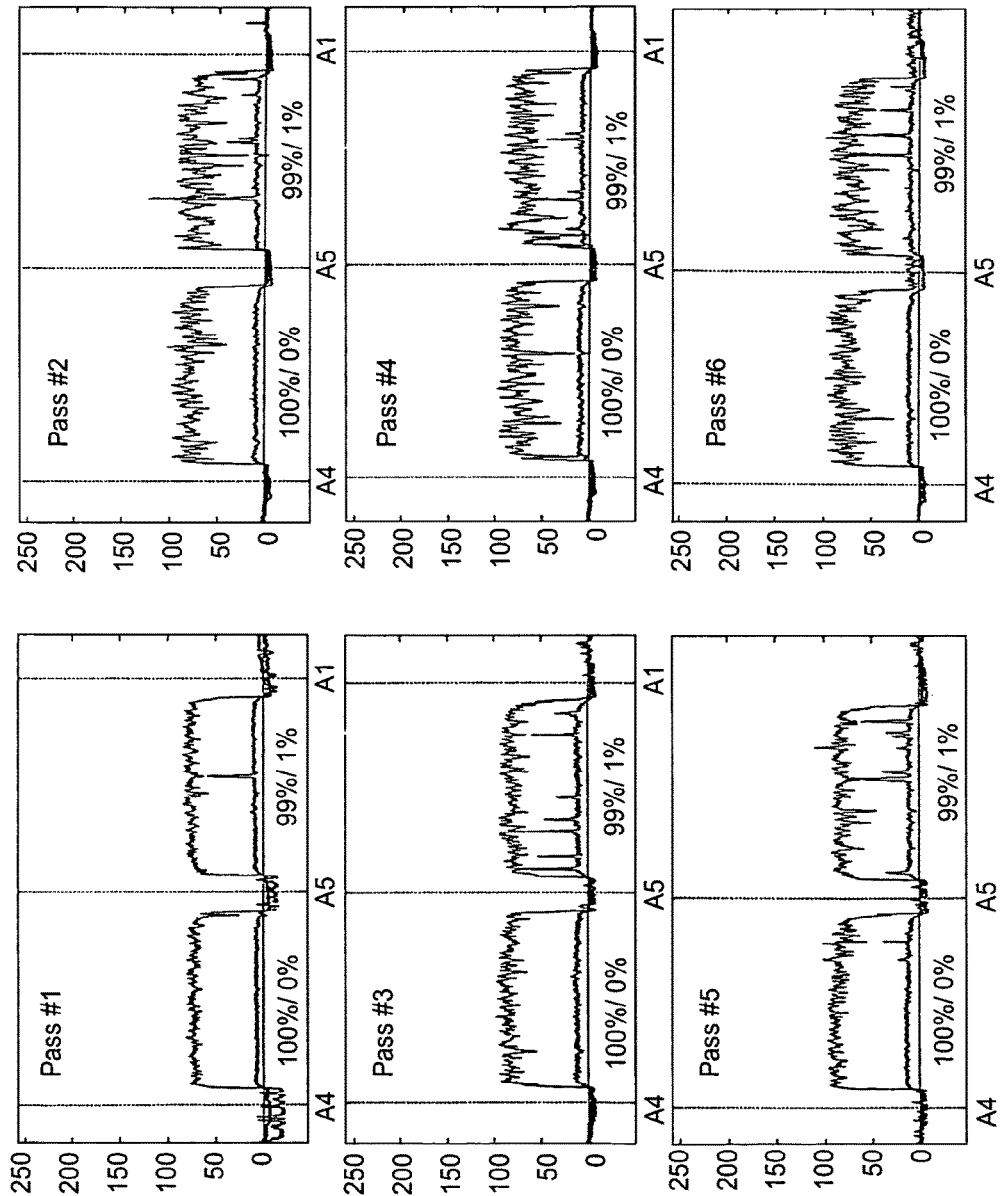
FIG. 11 is a data graph showing single molecule DNA amplification (6 passes).
Figure 12:
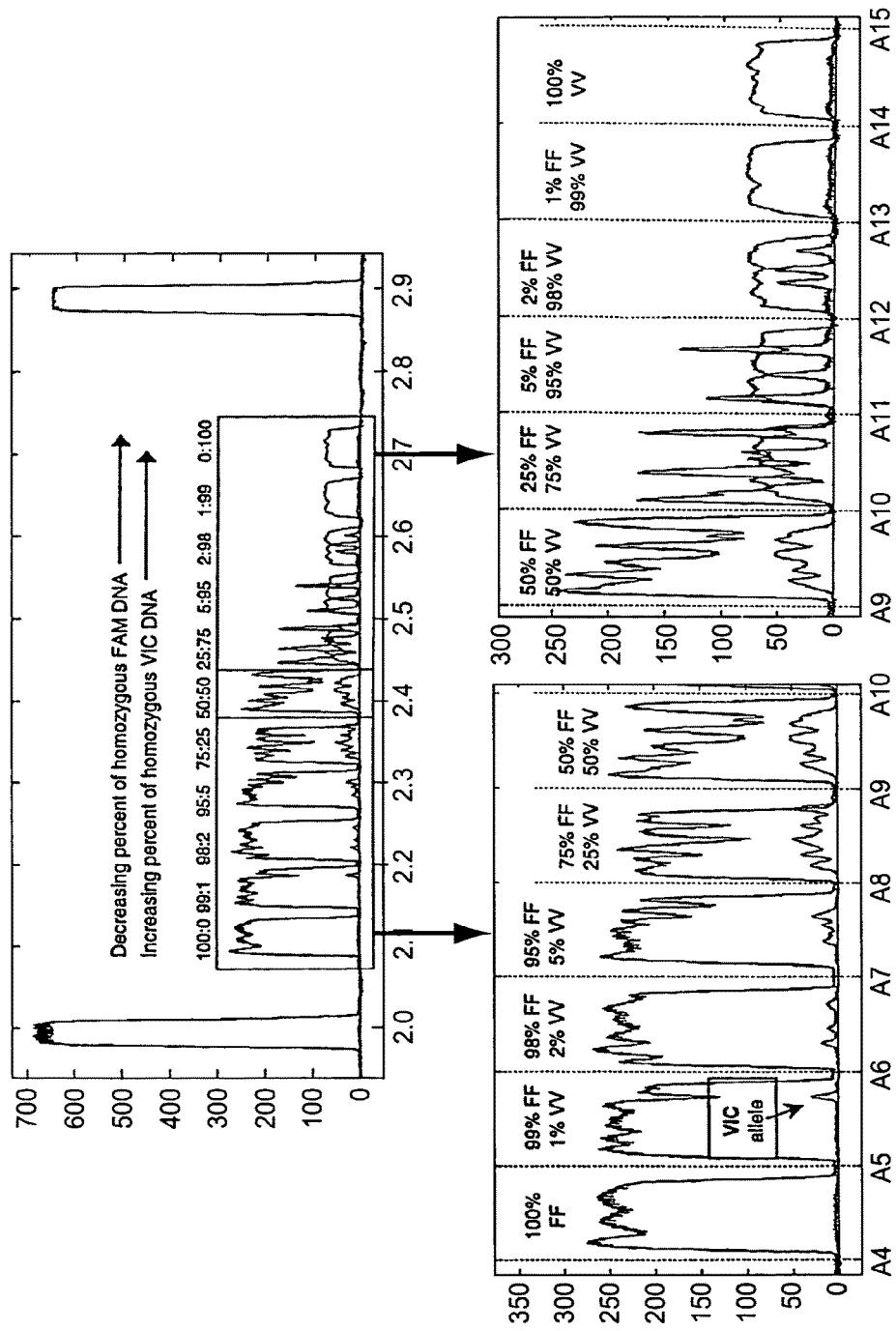
FIG. 12 is a data graph showing single molecule DNA amplification (3 panels).

FIGS. 10-12 show additional data from additional experimental runs, demonstrating single molecule amplification. As shown in FIGS. 10-11, a first set of experimental data with 100% of a first SNP allele is shown on the left, while a second set of experimental data with 1% of a second SNP allele (and 99% of the first allele) is shown on the right. The top signal line on the figure is data using a first dye detection system (which provides a "red" signal) for detecting amplification of the first allele, while the bottom line is data from a second dye detection system (a "blue" signal) for detecting amplification of the second allele. The data represents about 700 total detected DNA molecules in one sample slug. As shown, only the right side shows signal peaks corresponding to amplification of the second SNP. The data prove that a system of the invention can accurately amplify and detect rare molecules within a large population. That is, as a model, two DNA samples were mixed, each homozygous for the two alleles of a SNP. In this experiment, single DNA molecules for one allele that were present in a large population of DNA molecules of the other allele were detected (5-7 low copy alleles in about 700 for this case). FIG. 11 provides results for 6 separate experimental runs, demonstrating that characteristic peak shapes from molecule to molecule is constant, providing experimental evidence that both PCR and dispersion of the resulting amplicons are very reproducible. In fact, a LabChip®-based system, as in the present invention, allows unlimited sensitivity to rare molecules in that: 1) it is practical, in a microfluidic system, to spread the sample out through the channel such that rare molecules are present amongst smaller numbers of wild-type molecules (reducing the problems created by proportional amplification of starting materials in each aliquot); and 2) reproducible fluidic handling and analysis gives a predictable single molecule peak shape that can be used to discriminate between molecular signals and random signal fluctuations.

FIG. 12 provides a titration of a first SNP against a second SNP, showing that the signal from the amplicons corresponding to the first SNP ("FAM DNA," in the upper trace) and the second SNP ("VIC DNA," lower trace) show an appropriate signal correlation. The given percentages correspond to the percentage of DNA from a first homozygous sample (both alleles in the first homozygous sample are "FAM", that is, the material from the homozygous sample is "FF" homozygous) and a second homozygous sample (both alleles in the are VIC DNA sample, "VV"). In this context, "FAM DNA" stands for a DNA sequence that is probed for by a specific oligo sequence with a FAM dye label, while "VIC DNA" stands for a DNA sequence that is probed for by a specific oligo sequence with a VIC dye label. "FF" stands for a homozygous DNA sample for the "FAM" (oligo) sequence and "VV" stands for a homozygous DNA sample for the "VIC" (oligo) sequence.

Demonstration of Detection of Cancer Markers

Figure 13:
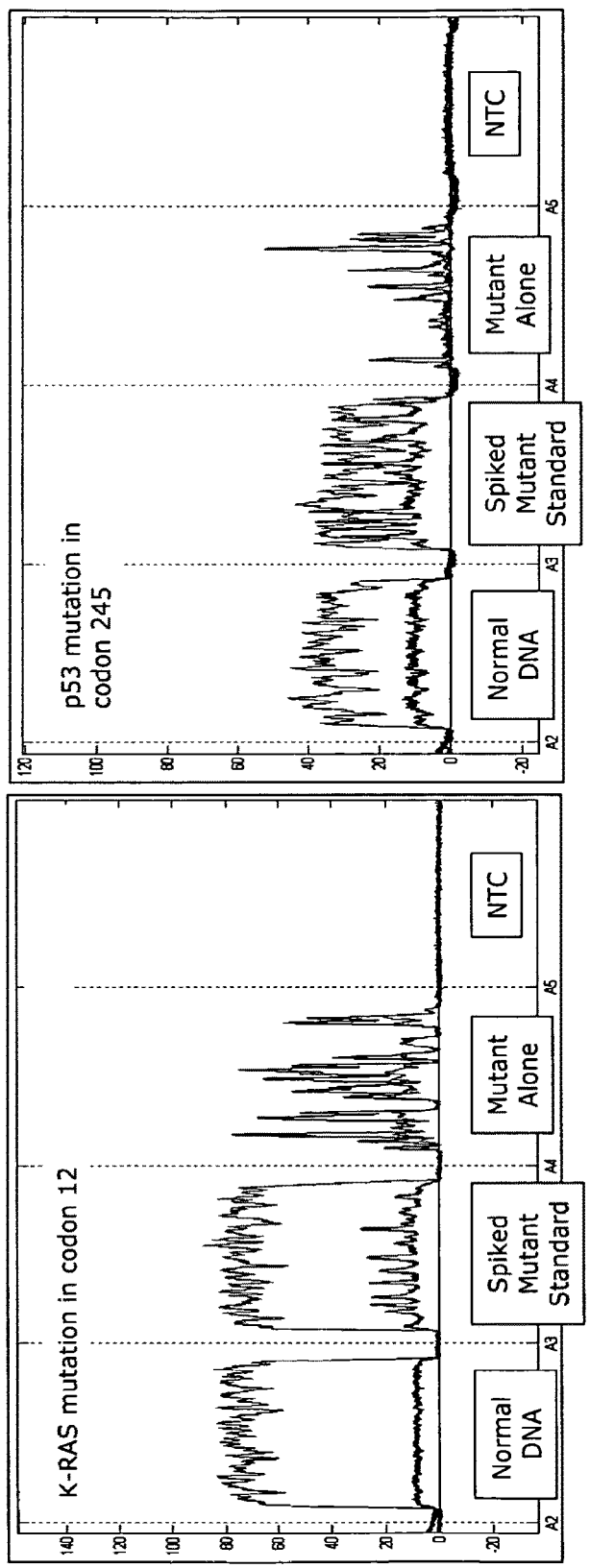
FIG. 13 provides a graph of detection of 2 mutation sites relevant to cancer detection developed on-chip using TaqMan probes.

FIG. 13 provides an example of detection of 2 mutation sites relevant to cancer detection developed on-chip, using TaqMan probes. To demonstrate the relevance of the system of the invention to cancer diagnostics, it was used to test a number of cancer (e.g., colorectal cancer) markers using TaqMan probes. Two of those assays are shown in FIG. 13: one for the K-RAS gene and one for the p53 gene, both diagnostic markers for a variety of cancers, such as colon cancer. The data trace shows fluorescence at two wavelengths vs. time for one microfluidic channel. Two TaqMan probes, one specific for the normal allele, and one specific for the mutant allele, were designed and tested in this on-chip assay format. The presence of normal DNA is detected with the wild-type probe (a "red" signal, designated in the black and white reproduction on the top data trace) and mutant DNA molecules are detected with the mutant probe (a "blue" signal, represented in the black and white reproduction as the bottom data trace). Most of the DNA molecules (approximately 500) in the sample slug are normal, shown by the high "red" top fluorescent signal and low "blue" bottom fluorescent signal. This signal is produced by the allele-specific (red, top) and background (blue, bottom) TaqMan probe cleavage surrounding the amplification products of normal genomic DNA molecules. When a mutant molecule (synthetic DNA template with the appropriate point mutation) traverses the system, it is amplified and recognized as a large blue (bottom) peak (with red (top) background peaks).

A Device and Method of Single Molecule Amplification by Microfluidics that Permits Accurate Analysis of Heterogeneous Nucleic Acid Mixtures.

Continuous flow PCR systems allow for spatial separation of different amplification reactions in a microfluidic processing environment. Normally, spatial separation is used to separate different reactions, where the starting template concentration is high enough to ensure accurate representation of alleles coming from both parents (e.g., about 50 genome equivalents are often used). In the present invention, the same task is accomplished by diluting the DNA enough such that individual template molecules are separated such that the amplification and detection products for each one are fluidically separated. If the detection product is allele specific, a signal for only one of the two alleles is detected. One can the count the results for each allele, giving the genotype quite accurately. The disadvantage for genotyping by this method is that the throughput decreases: one needs many reactions to get a genotype, instead of just one. Genotyping is typically performed with one reaction because the starting concentrations in a two allele system is usually about 50/50 (or at least on the same order of magnitude) and the signal-to-noise ratio of the genotyping biochemistry is good.

If, however, the representation of different alleles in the starting sample differs enormously, the genotyping biochemistry is not good enough to give an accurate quantitation of the under-represented allele. In fact, as a practical matter, it is very difficult to use many typical detection biochemistries for detection of alleles that are present in few as 1 in 5 copies. In cancer, the mutant/normal ratio can be quite low (1 in thousands) and therefore undetectable by conventional biochemical methods. On the other hand, if one amplifies single molecules, the reactions can be repeated and flowed in a continuous system for as long as desired—and there is no theoretical limit of detection (just a practical one: if the mutant genotype is very rare, many reactions will have to be performed in the continuous flow format).

This also provides a strategy for quantifying infectious agents by PCR. Today, that is done by PCR or RT-PCR which depends on a cycle-by-cycle quantification and comparison to a standard curve of template molecules amplified under similar conditions. In the present invention, we flowed the sample at a known flow rate and measured the amplifications per unit volume as a more precise and quantitative determination of the template concentration. One can accomplish the same thing by amplifying dilute concentrations of the sample in wells. When the total number of positive wells equaled $e^0=0.37$, there was a high statistical probability that each well had only a single template molecule in it. One could also have more than one molecule present in the flow stream at any given time if an independent and reliable way of measuring the copy number is used.

Single Molecule PCR in a Microfluidic Device Under Stop-Flow Conditions for Virus Detection & Analysis.

The desired sensitivity for virus detection (e.g., about 50-100 copies/ml) make it a challenging application for detection using a microfluidic platform, due to the mismatch between processing volume on the chip and the initial sample volume. However, one of the features of PCR in a microfluidic device demonstrated in this application is the ability to quantitate single copies of nucleic acids. This allows one to count the number of infected cells, or virus particles in a sample of interest, at biologically relevant concentrations of cells or virus particles. In this example, we describe quantitative single molecule PCR from a starting volume on the order of 10 microliters (an initial pre-concentration step taking the sample from ~1 ml to about 10 ul is performed by standard techniques, e.g. immunoprecipitation in the presence of magnetic beads).

The ~10 ul of concentrated solution containing e.g., >50 virus particles can be completely processed (or a substantial fraction of the volume) on a microfluidic chip in the following manner. The sample is mixed on-chip with the reagents necessary for PCR (at, e.g., a 1:1 ratio), e.g. primers, probes, dNTPs, etc. The mixture is pressure loaded into a microfluidic network that has a holdup volume on the order of 10 ul (see, FIG. 8), and the flow is stopped. As shown, the schematic device of FIG. 8 comprises PCR reagent well 801, sample well 802 vacuum/waste well 803, imaging area 804 and microfluidic network 805. The contents of the network are then thermocycled by applying heat externally to the chip, or, optionally, via resistive or Joule heating. Upon completion of thermocycling, the chip is imaged to located all of the "clouds" of fluorescence (see, FIG. 9), each corresponding, typically, to a single copy of DNA from a virus particle.

Figure 8:
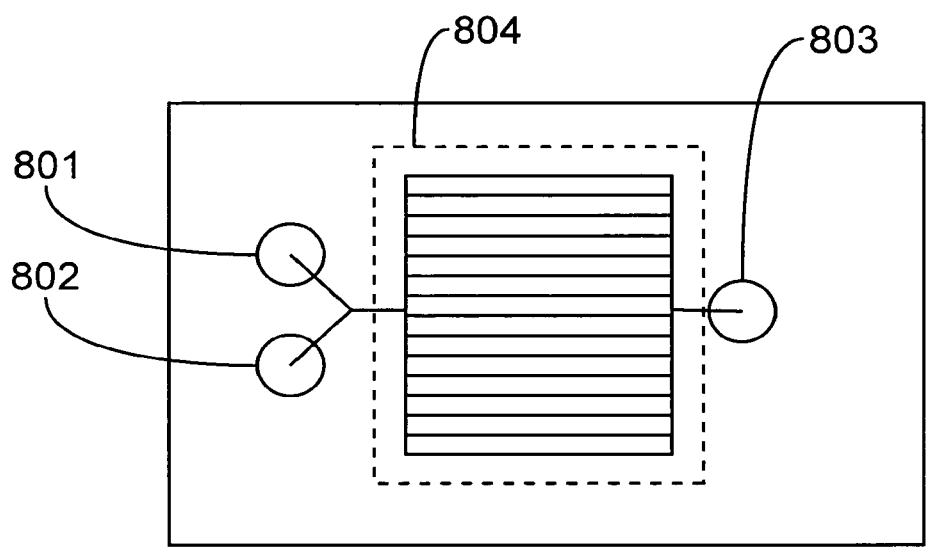
FIG. 8 is a schematic representation of a stopped flow system that uses simultaneous image processing of a network of channels to scan for nucleic acids of interest.
Figure 9:
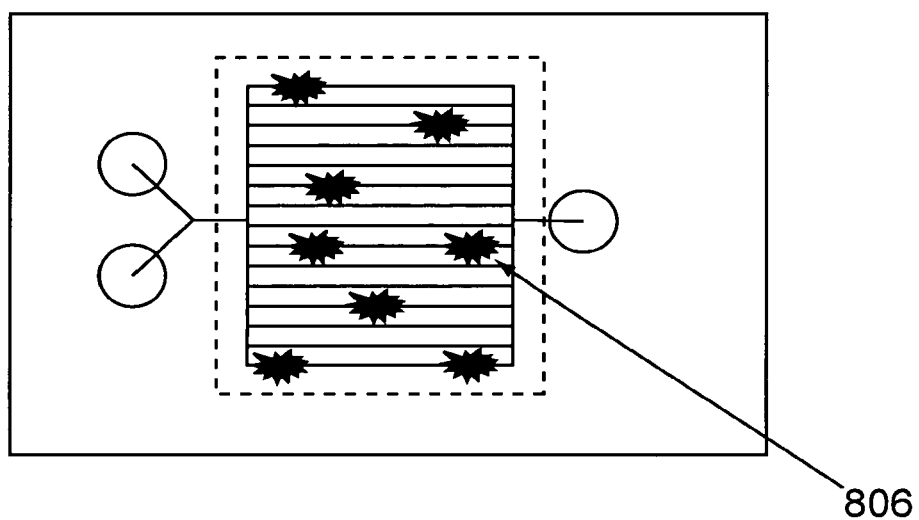
FIG. 9 is a schematic of a fluidic network after thermocycling. Spots represent the fluorescence "clouds" from single copy amplification reactions. The spots are counted for quantitative PCR analysis.

FIG. 9 is a schematic of the fluidic network of FIG. 8 after thermocycling. Spots 806 represent the fluorescence "clouds" from single amplicons (e.g., in one example, virus particle amplicons). Spots 806 can be counted for quantitative PCR. For this particular application, it is likely that it is most efficient to image the entire fluidic network of the chip simultaneously, rather than in a continuous flow mode with the detector at fixed points. However, continuous flow can, alternatively, be used. The active area of the chip for imaging is typically on the order of 20×30 mm (but can, optionally, be smaller or larger). This area is compatible with high resolution imaging (~1-2 um resolution) via techniques commonly used for DNA array applications. These can include CCD imaging, confocal laser scanning, and/or the like.

The dynamic range for quantification is typically at least 2-3 orders of magnitude, depending, in part, on the size of the chip. For a typical size of 20×30 mm, the dynamic range is about 2 orders of magnitude. One way to estimate the dynamic range is to examine the average separation between copies, and then compute the expected diffusion distances over the course of an experiment. A rough calculation to demonstrate that these types of volumes can be processed on a microfluidic chip is presented below.

To determine whether further concentration of a 10 uL sample down to the nL range was necessary, the following calculation was performed. The conclusion reached was that further concentration is not necessary.

If one loads a series of parallel channels (e.g., 64) that are 30 um deep, 120 um wide, and 30 mm long, the total volume in these channels is 6.2 μL. If it is further assumed that in the 6.2 μL, half of the volume comes from PCR reagents and the other half comes from the original 10 μL sample, then roughly 3 μL out of 10 μL are sampled per run, which is a reasonable volume from a statistical sampling and a practical ease of use standpoint. Furthermore, if the 10 μL concentrated sample contains 100 particles from an initial starting 1 mL volume of plasma, then one can detect about 30 PCR clouds per run, if the PCR efficiency is close to 100%. These clouds would be 62 mm apart, on average, from each other along the channel, or about 1 cloud in every 2 channels.

The next issue addressed is chip size and detection practicality. If the 64 (2^n binary split) parallel channels are packed together with 200 um landing area between, they will occupy 21 mm. So one images (or scans) an area of 30 mm×21 mm to find the 30 PCR clouds (in stop flow mode) that should appear in the channels. This is similar to the size of a typical DNA chip, meaning that available chip scanners can be used for the detection.

In summary, if 1 mL is concentrated to 10 μL and placed into a chip well, further concentration is unnecessary for detection. If anything is done to increase the volume (such as the addition of neutralization chemical(s) to an elution buffer, addition of lysing agents, etc.), a further concentration step can be desirable. To avoid adding lysing agents, it can be desirable to do an ultrasonic lysing of particles in the 10 μL solution in the well.

The following is one example protocol for quantitative analysis by the above methods: 1. Off chip concentration, e.g., by affinity capture (a standard technique) and elution to reduce the sample from 1 mL to 10 μL; 2. Place 10 μL in chip well, apply ultrasonic power to lyse particles; 3. Load DNA sample into parallel channels with on chip addition of PCR reagents by pressure, then stop flow; 4. Activate external heater to perform PCR in stop flow mode for all channels; and 5. Image or scan the channel to detect signs of single molecule PCR.

One aspect of the invention provides methods to ensure stopped flow conditions on a chip. There are a number of methods that can be employed. For example, one can use temperature sensitive materials (e.g. polymers), to create the stop-flow condition. A simple method to achieve stopped flow is to use standard chip-capillary or chip-tubing connections combined with a valve.

While the foregoing invention has been described in some detail for purposes of clarity and understanding, it will be clear to one skilled in the art, from a reading of this disclosure, that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting a nucleic acid of interest, the method comprising:
   aliquotting a sample comprising the nucleic acid of interest and one or more additional nucleic acids into a plurality of reaction mixtures, wherein at least one of the plurality of reaction mixtures is a single copy reaction mixture comprising a single copy of the nucleic acid of interest, wherein the plurality of reaction mixtures additionally comprise at least one additional reaction mixture comprising at least one copy of the additional nucleic acid;
   simultaneously subjecting the plurality of reaction mixtures in parallel to one or more amplification reactions while flowing each of the plurality of reaction mixtures through one of a plurality of channels of a microfluidic device; and,
   detecting the nucleic acid of interest in the at least one single copy reaction mixture;
   wherein at least one of the plurality of reaction mixtures is formulated in an aqueous phase of an emulsion comprising aqueous droplets suspended in and surrounded by an immiscible liquid.

2. The method of claim 1, wherein the amplification is performed on the plurality of reaction mixtures formulated in the emulsion.

3. The method of claim 2, wherein the nucleic acid of interest is present as a single copy in at least one aqueous droplet of the aqueous phase prior to performing the amplification reaction.

4. The method of claim 2, wherein the nucleic acid of interest is detected in the emulsion after the amplification reaction is performed.

5. The method of claim 2, wherein a plurality of additional nucleic acids are also formulated in the aqueous phase of the emulsion, and the method comprises detecting the plurality of additional nucleic acids.

6. The method of claim 1, wherein the nucleic acid of interest is continuously flowed during a plurality of steps of the method.

7. The method of claim 1, wherein the aliquotting comprises flowing the sample into a microfluidic dilution channel or chamber and diluting the sample in the microfluidic dilution channel or chamber, whereby the sample is aliquotted into multiple diluted aliquots in the microfluidic dilution channel or chamber.

8. A method of detecting a low copy nucleic acid of interest in a sample that comprises a higher copy additional nucleic acid that is different from the low copy nucleic acid, the method comprising:
   aliquotting the sample into a plurality of reaction mixtures, which reaction mixtures comprise a plurality of zero copy reaction mixtures comprising zero copies of the nucleic acid of interest and at least one single copy reaction mixture comprising a single copy of the nucleic acid of interest;
   simultaneously subjecting the zero and single copy reaction mixtures in parallel to an amplification reaction while flowing each of the plurality of reaction mixtures through one of a plurality of channels of a microfluidic device;
   detecting the nucleic acid of interest in the single copy reaction mixture;
   wherein at least one of the plurality of reaction mixtures is formulated in an aqueous phase of an emulsion comprising aqueous droplets suspended in and surrounded by an immiscible liquid.

9. The method of claim 8, wherein the amplification is performed on the zero and single copy reaction mixtures formulated in the emulsion.

10. The method of claim 9, wherein the nucleic acid of interest is present as a single copy in at least one aqueous droplet of the aqueous phase prior to performing the amplification reaction.

11. The method of claim 9, wherein the nucleic acid of interest is detected in the emulsion after the amplification reaction is performed.

12. The method of claim 9, wherein the higher copy additional nucleic acid that is different from the low copy nucleic acid is also formulated in the aqueous phase of the emulsion and the method comprises detecting the plurality of additional nucleic acids.

13. The method of claim 8, wherein the aliquotting comprises flowing the sample into a microfluidic dilution channel or chamber and diluting the sample in the microfluidic dilution channel or chamber, whereby the sample is aliquotted into multiple diluted aliquots in the microfluidic dilution channel or chamber.

14. The method of claim 5, further comprising determining concentration of the nucleic acids of interest in the emulsion from a ratio of the detected plurality of additional nucleic acids to the detected nucleic acid of interest.

15. The method of claim 12, further comprising determining concentration of the nucleic acids of interest in the emulsion from a ratio of the detected plurality of additional nucleic acids to the detected nucleic acid of interest.

* * * * *